United States Patent
Chen et al.

(10) Patent No.: US 9,445,930 B2
(45) Date of Patent: Sep. 20, 2016

(54) METHODS, DEVICES, AND SYSTEMS FOR OBESITY TREATMENT

(71) Applicant: FULFILLIUM, INC., Napa, CA (US)

(72) Inventors: Richard D. Y. Chen, Napa, CA (US);
Craig A. Johanson, Napa, CA (US);
Christopher S. Jones, Napa, CA (US);
Reinhold H. Dauskardt, Napa, CA (US); Marc B. Taub, Napa, CA (US)

(73) Assignee: FULFILLIUM, INC., Napa, CA (US)

( * ) Notice: Subject to any disclaimer, the term of this patent is extended or adjusted under 35 U.S.C. 154(b) by 0 days.

(21) Appl. No.: 14/971,795

(22) Filed: Dec. 16, 2015

(65) Prior Publication Data
US 2016/0100800 A1    Apr. 14, 2016

Related U.S. Application Data

(63) Continuation of application No. 11/282,224, filed on Nov. 18, 2005, which is a continuation-in-part of application No. 11/170,274, filed on Jun. 28, 2005, now Pat. No. 8,070,807, which is a continuation-in-part of application No. 11/122,315, filed on May 3, 2005, now Pat. No. 8,066,780.

(60) Provisional application No. 60/629,800, filed on Nov. 19, 2004.

(51) Int. Cl.
*A61F 2/04*    (2013.01)
*A61F 5/00*    (2006.01)
(Continued)

(52) U.S. Cl.
CPC .............. *A61F 5/003* (2013.01); *A61B 5/076* (2013.01); *A61B 5/686* (2013.01); *A61B 5/7282* (2013.01); *A61B 5/746* (2013.01); *A61F 2/12* (2013.01); *A61F 5/0036* (2013.01); *A61F 5/0046* (2013.01); *A61N 1/08* (2013.01); *G08B 21/18* (2013.01); *A61F 2/26* (2013.01);
(Continued)

(58) Field of Classification Search
CPC ........ A61F 5/003; A61F 5/0046; A61F 2/12; A61F 2250/0002; A61F 2210/0061; A61B 5/7282; A61B 5/686; A61B 5/076; A61B 5/746
See application file for complete search history.

(56) References Cited

U.S. PATENT DOCUMENTS 3,046,988 A    7/1962    Moreau et al.
3,055,371 A    9/1962    Kulick
(Continued)

FOREIGN PATENT DOCUMENTS

EP    0103481 A1    3/1984
EP    0246999 A1    11/1987
(Continued)

OTHER PUBLICATIONS

European Search Report and Search Opinion of EP Patent Application No. 05824820.4, mailed Mar. 4, 2010, 11 pages total.
(Continued)

*Primary Examiner* — Julian W Woo
(74) *Attorney, Agent, or Firm* — Oblon, McClelland, Maier & Neustadt, L.L.P.

(57) ABSTRACT

Upon filling multiple inflatable chambers of a gastric balloon structure in a patient's stomach, the gastric balloon structure assumes a natural three-dimensional kidney shape of the gastric cavity. A flexible central spine may span a gap between two inflatable chambers and may include lumens for inflation of one or both chambers. The plurality of compartments, when in an inflated state, may form a cavity therebetween through which food may pass and may leave in a stomach a residual volume of 10 ml to 100 ml.

30 Claims, 18 Drawing Sheets

(51) Int. Cl.
  *A61F 2/12* (2006.01)
  *A61N 1/08* (2006.01)
  *A61B 5/07* (2006.01)
  *A61B 5/00* (2006.01)
  *G08B 21/18* (2006.01)
  *A61F 2/26* (2006.01)
  *A61N 1/37* (2006.01)

(52) U.S. Cl.
  CPC  *A61F2210/0061* (2013.01); *A61F 2250/0002* (2013.01); *A61F 2250/0003* (2013.01); *A61F 2250/008* (2013.01); *A61N 1/3706* (2013.01)

(56) References Cited

U.S. PATENT DOCUMENTS

| | | | |
|---|---|---|---|
| 4,133,315 | A | 1/1979 | Berman et al. |
| 4,246,893 | A | 1/1981 | Berson |
| 4,311,146 | A | 1/1982 | Wonder |
| 4,416,267 | A | 11/1983 | Garren et al. |
| 4,455,691 | A | 6/1984 | Van Aken Redinger et al. |
| 4,485,805 | A | 12/1984 | Foster, Jr. |
| 4,501,264 | A | 2/1985 | Rockey |
| 4,517,979 | A * | 5/1985 | Pecenka ............ A61B 17/12109 606/195 |
| 4,598,699 | A | 7/1986 | Garren et al. |
| 4,607,618 | A | 8/1986 | Angelchik |
| 4,648,383 | A | 3/1987 | Angelchik |
| 4,694,827 | A | 9/1987 | Weiner et al. |
| 4,723,893 | A | 2/1988 | Kiyooka et al. |
| 4,739,758 | A | 4/1988 | Lai et al. |
| 4,795,463 | A | 1/1989 | Gerow |
| 4,824,436 | A * | 4/1989 | Wolinsky ................ A61B 17/22 604/101.03 |
| 4,899,747 | A | 2/1990 | Garren et al. |
| 4,908,011 | A | 3/1990 | Jacobsen et al. |
| 4,925,446 | A | 5/1990 | Garay et al. |
| 4,983,167 | A | 1/1991 | Sahota |
| 5,084,061 | A | 1/1992 | Gau et al. |
| 5,160,321 | A | 11/1992 | Sahota |
| 5,234,454 | A | 8/1993 | Bangs |
| 5,259,399 | A | 11/1993 | Brown |
| 5,308,317 | A | 5/1994 | Ferguson et al. |
| 5,400,770 | A | 3/1995 | Nakao et al. |
| 5,401,241 | A | 3/1995 | Delany |
| 5,501,667 | A | 3/1996 | Verduin, Jr. |
| 5,653,683 | A | 8/1997 | D'Andrea |
| 5,720,717 | A | 2/1998 | D'Andrea |
| 5,833,603 | A | 11/1998 | Kovacs et al. |
| 5,850,144 | A | 12/1998 | Howells et al. |
| 5,865,801 | A | 2/1999 | Houser |
| 5,993,473 | A | 11/1999 | Chan et al. |
| 6,254,570 | B1 | 7/2001 | Rutner et al. |
| 6,427,089 | B1 | 7/2002 | Knowlton |
| 6,454,785 | B2 | 9/2002 | De Hoyos Garza |
| 6,579,301 | B1 | 6/2003 | Bales et al. |
| 6,605,056 | B2 | 8/2003 | Eidenschink et al. |
| 6,656,194 | B1 | 12/2003 | Gannoe et al. |
| 6,733,512 | B2 | 5/2004 | McGhan |
| 6,736,793 | B2 | 5/2004 | Meyer et al. |
| 6,746,460 | B2 | 6/2004 | Gannoe et al. |
| 6,755,869 | B2 | 6/2004 | Geitz |
| 6,855,143 | B2 | 2/2005 | Davison et al. |
| 6,976,950 | B2 | 12/2005 | Connors et al. |
| 6,981,980 | B2 | 1/2006 | Sampson et al. |
| 6,994,095 | B2 * | 2/2006 | Burnett ................ A61F 5/0073 606/192 |
| 7,033,373 | B2 | 4/2006 | De la Torre et al. |
| 7,033,384 | B2 | 4/2006 | Gannoe et al. |
| 7,066,945 | B2 | 6/2006 | Hashiba et al. |
| 7,135,034 | B2 | 11/2006 | Friedman et al. |
| 7,141,071 | B2 | 11/2006 | Imran |
| 7,261,730 | B2 | 8/2007 | Friedman et al. |
| 7,449,026 | B2 | 11/2008 | Zalesky et al. |
| 7,753,928 | B2 | 7/2010 | de la Torre et al. |
| 8,066,780 | B2 | 11/2011 | Chen et al. |
| 8,070,807 | B2 | 12/2011 | Chen |
| 8,075,582 | B2 | 12/2011 | Lointier et al. |
| 8,142,469 | B2 | 3/2012 | Sosnowski et al. |
| 8,236,023 | B2 | 8/2012 | Birk et al. |
| 9,149,611 | B2 | 10/2015 | Bouasaysy |
| 2001/0001314 | A1 | 5/2001 | Davison et al. |
| 2001/0010024 | A1 | 7/2001 | Ledergerber |
| 2001/0020150 | A1 | 9/2001 | Ravo |
| 2002/0011934 | A1 | 1/2002 | Cacioli et al. |
| 2002/0055757 | A1 | 5/2002 | Torre et al. |
| 2003/0153905 | A1 | 8/2003 | Edwards et al. |
| 2003/0171768 | A1 | 9/2003 | McGhan |
| 2004/0044357 | A1 | 3/2004 | Gannoe et al. |
| 2004/0059289 | A1 | 3/2004 | Garza Alvarez |
| 2004/0106899 | A1 | 6/2004 | McMichael et al. |
| 2004/0122526 | A1 | 6/2004 | Imran |
| 2004/0122527 | A1 | 6/2004 | Imran |
| 2004/0162593 | A1 | 8/2004 | Jorgenson et al. |
| 2004/0162613 | A1 | 8/2004 | Roballey |
| 2004/0186502 | A1 | 9/2004 | Sampson et al. |
| 2004/0186503 | A1 | 9/2004 | LeLegge |
| 2005/0027246 | A1 | 2/2005 | Dion |
| 2005/0033331 | A1 | 2/2005 | Burnett et al. |
| 2005/0033346 | A1 | 2/2005 | Sater |
| 2005/0055039 | A1 | 3/2005 | Burnett et al. |
| 2005/0070937 | A1 | 3/2005 | Jambor et al. |
| 2005/0107664 | A1 | 5/2005 | Kalloo et al. |
| 2005/0119674 | A1 | 6/2005 | Gingras |
| 2005/0131500 | A1 | 6/2005 | Zalesky et al. |
| 2005/0159769 | A1 | 7/2005 | Alverdy |
| 2005/0181977 | A1 | 8/2005 | Hunter et al. |
| 2005/0192614 | A1 | 9/2005 | Binmoeller |
| 2005/0267405 | A1 | 12/2005 | Shah |
| 2005/0267595 | A1 | 12/2005 | Chen et al. |
| 2005/0267596 | A1 | 12/2005 | Chen et al. |
| 2005/0273060 | A1 | 12/2005 | Levy et al. |
| 2005/0288700 | A1 | 12/2005 | Chermoni |
| 2006/0004272 | A1 | 1/2006 | Shah et al. |
| 2006/0155259 | A1 | 7/2006 | MacLay |
| 2006/0178691 | A1 | 8/2006 | Binmoeller |
| 2007/0060940 | A1 | 3/2007 | Brazzini et al. |
| 2007/0100368 | A1 | 5/2007 | Quijano et al. |
| 2007/0100369 | A1 | 5/2007 | Cragg et al. |
| 2007/0118168 | A1 | 5/2007 | Lointier et al. |
| 2007/0135829 | A1 | 6/2007 | Paganon |
| 2008/0262529 | A1 | 10/2008 | Jacques |
| 2009/0048624 | A1 | 2/2009 | Alverdy |
| 2010/0100115 | A1 | 4/2010 | Soetermans et al. |
| 2010/0130998 | A1 | 5/2010 | Alverdy |
| 2013/0296765 | A1 | 11/2013 | Dominguez et al. |
| 2014/0257358 | A1 | 9/2014 | Alverdy |
| 2015/0150699 | A1 | 6/2015 | Pattison et al. |

FOREIGN PATENT DOCUMENTS

| | | |
|---|---|---|
| EP | 1177763 A | 2/2002 |
| EP | 1 929 957 A1 | 6/2008 |
| GB | 2090747 A | 7/1982 |
| GB | 2139902 A | 11/1984 |
| GB | 2384993 A | 8/2003 |
| WO | 83/02888 A1 | 9/1983 |
| WO | 87/00034 A2 | 1/1987 |
| WO | 88/00027 A1 | 1/1988 |
| WO | 97/33513 A1 | 9/1997 |
| WO | 02/35980 | 5/2002 |
| WO | 03/055420 | 7/2003 |
| WO | 03/095015 A1 | 11/2003 |
| WO | 2005/107641 A2 | 11/2005 |
| WO | WO 2005/112822 A1 | 12/2005 |
| WO | WO 2011/028886 A1 | 3/2011 |
| WO | WO 2013/039412 A1 | 3/2013 |
| WO | WO 2014/055766 A1 | 4/2014 |

OTHER PUBLICATIONS

Office Action of Japanese Patent Application No. 2007-53307, mailed May 18, 2010, 7 pages total (English Translation Included).
Office Action dated Mar. 11, 2010 for U.S. Appl. No. 11/170,274.

(56) References Cited

OTHER PUBLICATIONS

Office Action dated Apr. 15, 2011 for U.S. Appl. No. 11/170,274.
Office Action dated Jul. 29, 2009 for U.S. Appl. No. 11/170,274.
Office Action dated Dec. 7, 2010 for U.S. Appl. No. 11/170,274.
Office Action dated Dec. 24, 2008 for U.S. Appl. No. 11/170,274.
Notice of Allowance dated Oct. 27, 2011 for U.S. Appl. No. 11/170,274.

* cited by examiner

FIG. 15D
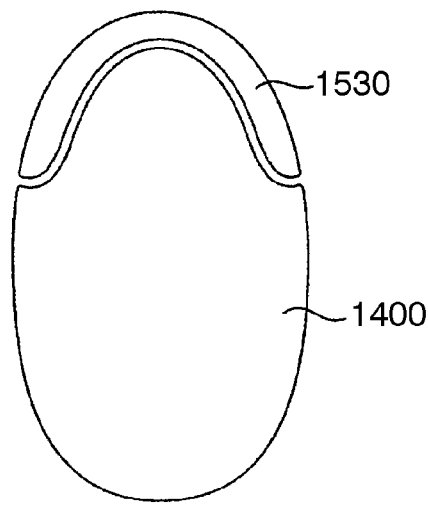
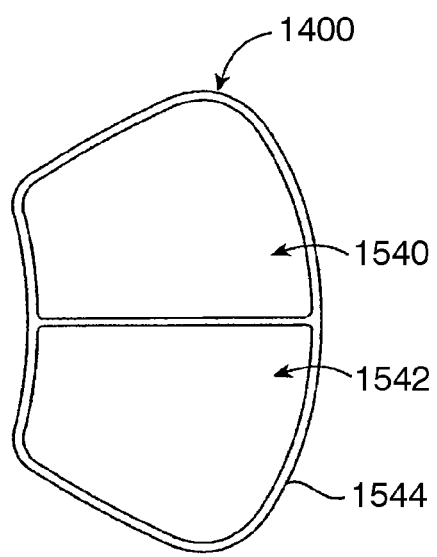
FIG. 15E
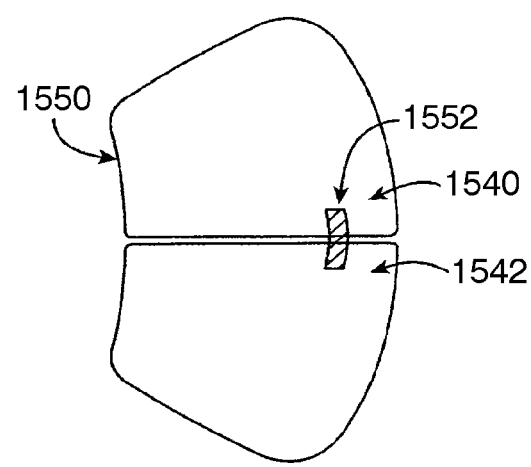
FIG. 15F

METHODS, DEVICES, AND SYSTEMS FOR OBESITY TREATMENT

CROSS-REFERENCES TO RELATED APPLICATIONS

This application is a continuation of and claims the benefit of priority from U.S. patent application Ser. No. 11/282,224, filed Nov. 18, 2005, which is a continuation-in-part of application Ser. No. 11/170,274, filed on Jun. 28, 2005 and issued Dec. 6, 2011 as U.S. Pat. No. 8,070,807 entitled "Wireless Breach Detection", which was a continuation in-part of application Ser. No. 11/122,315, filed on May 3, 2005 and issued Nov. 29, 2011 as U.S. Pat. No. 8,066,780 entitled "Methods for Gastric Volume Control", and claims the benefit under 35 USC §119(e) of prior provisional application No. 60/629,800, filed on Nov. 19, 2004, the full disclosures of which are incorporated herein by reference.

BACKGROUND OF THE INVENTION

1. Field of the Invention

The present invention relates generally to medical apparatus and methods. More particularly, the present invention relates to implantable devices and methods and systems for detecting their malfunction or failure or impending malfunction or failure.

All implants of devices, especially those indicated for long term use, in the human body are highly regulated and must meet certain safety requirements. One such requirement is biocompatibility of the materials used in the construction of the device in the event they come into direct contact with body tissues and fluids. Even if the material is biocompatible, the contact with body tissues and fluid could result in diminished performance or malfunction esp. in devices with electronic components. It is known that when a device is implanted in the body, the materials forming the cover and structural elements of the device degrade and fatigue over time. It is also well known that excessive handling during implantation or even normal, repetitive movements could stress the structural integrity of the device. Failure of the structural integrity of the device or its covering, which eventually happens, causes the contents of the device, which heretofore were confined in the interior of the device, to be in contact with the surrounding tissues and their secretions. Therefore, it would be desirable to detect or to predict such an event before any potentially harmful contents come in contact with the surrounding tissues, before tissue secretions leak into the interior of the device resulting in malfunction, or before the content itself suffers a malfunction.

Prosthetic devices implanted in numerous locations in the body are prevalent in medical practice. Many of these prostheses are designed to assume the structural shape of the body part yet are soft and have similar flexibility to approximate the look and feel of normal human tissue. A common use has been for reconstructing the normal contour, improving the shape, and/or enlarging the size of the human breast. The most common breast prosthesis is a soft elastomeric container made of silicone rubber which is filled or "inflated" with a liquid or gel, typically a saline solution or a silicone gel, or a combination of such filling materials. Typically such prostheses are surgically implanted to fit underneath the skin of the body either between the chest wall and the mammary gland or in place of the mammary gland following a mastectomy. The ideal result after implantation is to achieve the contours and tissue characteristics of a natural breast, and prosthetic devices filled with silicone gel have been found to produce the best cosmetic result. Hence, silicone gel breast implants are the devices of choice in locations where they are approved.

Degradation and fatigue of the silicone rubber container of such breast implants, however, can lead to perforations, tears, ruptures, and seam separations, resulting in the leakage of filling materials to the surrounding tissues. Leakage from a saline filled device is usually harmless as the solution, if uncontaminated, is absorbed. Leakage from the preferred silicone gel filled device is much more problematic. Bleeding of gel at the surface is believed to contribute to the development of capsular contracture, a scarring condition that compresses the implanted device from a soft, natural profile into a rigid, spherical shape. More serious is the migration of leaked silicone gel to other parts of the body such as the lymph nodes and major organs where it becomes unremovable. Consequently, silicone gel has been implicated in many health problems including connective tissue diseases. This risk increases with the length of time the device is implanted.

The problem is exacerbated by the fact that leakage of silicone gel is not easily detected and the rupture of the device cannot be predicted. Unlike saline filled devices where rupture and leakage results in deflation over a short period of time and readily discovered by the patient, silicone gel tends to leak slowly and can go unnoticed for years. Often the rupture is discovered only upon removal of the device for another reason. The only noninvasive method currently sensitive enough to detect such an event reliably is an MRI scan. To monitor the integrity of a silicone gel device by regularly scheduled MRI scans is cost prohibitive. Consequently, the use of silicone gel filled breast prostheses is now highly restricted by regulatory authorities.

Gastric balloons are another type of implantable, inflatable prosthesis which is subject to failure from breach of the wall. Gastric balloons are typically introduced through the esophagus and inflated in situ in order to occupy a significant volume within the stomach. While gastric balloons are typically inflated with saline or other non-toxic materials which are benign if released into the stomach, the balloon structure itself is hazardous if accidentally deflated since it can pass and cause obstruction of the pyloric valve or the intestines distal to the pyloric valve. Any such obstruction is a medical emergency.

The problem is not limited to inflatable devices. Many implanted devices, e.g., cardiac pacemakers, contain electronic circuits and have insulated wires or leads that sense or deliver signals at certain points in the body. For example, the covering or insulation could deteriorate over time or tear in response to normal body movements. Body fluids from the surrounding could then leak into the circuitry, either as a liquid or vapor, causing disruption of signals. Or the lead could break at any point or detach from the connector to the device. Another class of implanted devices involves a closed vessel system conveying fluids leading from a part of the device or a part of the body to another part of the body, such as a shunt conveying blood or cerebrospinal fluid. The catheter or reservoir in the system could tear or break leading to the leakage of material out of the catheter to an unintended part of the body or leakage of body fluids into the catheter causing contamination. Yet another class of devices, which depend on solid objects for function or structural support, could fail from fracture or dislocation. These fractures can start as a hairline from repeated mechanical stress from use and progress to a complete fracture. Dislocations start with a loosening of the structure(s) holding an object in place and progress to a complete dislocation.

For these reasons, it would be desirable to provide apparatus and methods to detect or predict an actual or potential wall breach which can lead to leakage of the filling contents of breast implants, gastric balloons, catheters, reservoirs, and the like or an actual or potential disruption of an electronic circuit in cardiac pacemakers or neurostimulators or the like or an actual or potential stress fracture or dislocation in the case of solid components in prosthetic devices or the like. It would desirable further to monitor remotely the structural integrity and presumed functional status of a device without activating the function after device implantation in the case of cardiac defibrillators or without directly applying stress to the monitored part in the case of solid components. Prompt removal of such devices upon breach or imminent breach would avert most, if not all, of the ensuing problems including catastrophes. The methods and apparatus will preferably be adaptable for use in any structural design of the device without adversely affecting its structure or, in the case of breast implants, the final cosmetic result, and further be applicable to solid and rigid body implants containing electronic components such as pacemaker and defibrillator canisters and leads and to solid body implants such as prosthetic heart valves or orthopedic devices. It would be further desirable if the breach or imminent breach of the device were detectable to the patient in an easy, rapid, and reliable fashion outside of a medical facility or at home. Additionally, it would be beneficial if the system were able to monitor the device non-invasively on a frequent basis over the life of the device without incurring significant additional cost for each diagnostic event. At least some of these objectives will be met by the inventions described hereinafter.

2. Description of the Background Art

Leakage detection is described in U.S. Pat. No. 6,826,948 and published applications US 2004/0122526 and US 2004/0122527. Breast implants and methods for their use are described in U.S. Pat. Nos. 6,755,861; 5,383,929; 4,790,848; 4,773,909; 4,651,717; 4,472,226; and 3,934,274; and in U.S. PubL Appln. 2003/163197. Gastric balloons and methods for their use in treating obesity are described in U.S. Pat. Nos. 6,746,460; 6,736,793; 6,733,512; 6,656,194; 6,579,301; 6,454,785; 5,993,473; 5,259,399; 5,234,454; 5,084,061; 4,908,011; 4,899,747; 4,739,758; 4,723,893; 4,694,827; 4,648,383; 4,607,618; 4,501,264; 4,485,805; 4,416,267; 4,246,893; 4,133,315; 3,055,371; and 3,046,988 and in the following publications: US 2005/0137636; US 2004/0215300; US 2004/0186503; US 2004/0186502; US 2004/0162593; US 2004/0106899; US 2004/0059289; US 2003/0171768; US 2002/0099430; US 2002/0055757; WO 03/095015; WO88/00027; WO87/00034; WO83/02888; EP 0103481; EP0246999; GB2090747; and GB2139902.

BRIEF SUMMARY OF THE INVENTION

The present invention provides systems and methods for detecting partial or complete breach in the exterior wall of an implantable device, such as an inflatable, implantable prosthesis of the type where a wall at least partially surrounds a fluid medium, liquid or air, in one or more inflatable compartments. The walls of inflatable devices will usually be non-rigid, either elastic or non-elastic. Other implantable devices subject to exterior structure breach include metal and plastic (polymer) devices which may comprise rigid-walled casings or housings, such as pacemakers, implantable defibrillators, neurostimulators, insulin pumps, reservoirs, devices having flexible housings such as elastomeric reservoirs containing with naturally collected or pre-filled fluids or insulation or other coverings formed over the electrically conductive core of electrical leads, electrical connectors (e.g., plugs), and the like. Implantable devices subject to stress fracture in solid functional components include artificial joints, prosthetic heart valves, and the like. These and other devices may contain potentially bioincompatible materials, such as batteries, circuitry, synthetic chemicals, and the like. While the implementation of these systems and methods will be described in detail in connection with inflatable devices such as breast implants and gastric balloons and with solid core devices such as electrical leads, it will be appreciated that the principles may be applied to other inflatable prostheses, such as penile implants, to vessel systems containing or conveying fluids, to electronic and other devices having solid internal structural or functional components. The systems of the present invention are incorporated into at least a portion of the wall of the wall or covering of the inflatable prosthesis or other device or coupled to the electronic circuitry or embedded in the solid component itself and provide for or enable the emission or transmission of a detectable radio-frequency or other electronic signal upon breach or partial breach of the wall or the structural integrity of the component. As used hereinafter, the term "breach" will refer to any partial or full penetration of the structure of the wall or covering as well as to other mechanical disruption of a solid part of the device which could initiate or lead to the contact of materials inside the wall or covering or the solid component itself with tissues or body fluids outside the device. Such breach signifies a compromise or a threatening compromise to the integrity of the device.

The signal emission system of the present invention preferably comprises a signaling circuit having one or more components which become exposed to an exterior or interior environment surrounding or within the prosthesis or other implantable device upon breach or partial breach of the wall or covering, wherein such exposure enables, disables, energizes, and/or changes a signal which is emitted by the system. In particular, the breach may act like a switch to close or open a region within the signaling circuit to cause, enable, disable, or alter the signal emission. Alternatively, the exposure of the circuit and/or internal structure to the interior or exterior environment may result in a change in impedance, capacitance, inductance or other detectable circuit characteristics that can trigger or modify the signal emitted.

In a first embodiment, the component of the signaling circuit will generate electrical current when exposed to a body fluid and/or an interior medium within the device upon breach or failure of the exterior structure. Body fluids such as blood, cerebrospinal fluid, lymph fluid, and the like, are naturally conductive, i.e., contain electrolytes. The interior medium, such as an inflation medium, can be selected to be electrically conductive, e.g., comprise or consist of saline or other biologically compatible electrolytes and salt solutions. In such cases, the generated electrical current can power an unpowered transmission component to emit the signal. Alternatively, the power can alter a signal which has already been continuously or periodically emitted by the signaling circuit. In the latter case, the signaling circuit may require a separate source of energy, such as a battery or circuit components which are placed on the exterior or interior of the wall so that they are always exposed to fluids to provide for current generation.

Alternatively, the circuit components may include spaced-apart conductors which are electrically coupled to the signaling circuit to "close" the signaling circuit to permit current flow when exposed to a body fluid and/or device contents by a wall breach. Alternatively, the circuit may be altered, enabled or otherwise modified by a sufficient flow of electrolytes to enable, interpret, disrupt, or modify a signal emission. The circuit components may include spaced apart conductors which are coupled to the signaling circuit to detect a change in resistance, capacitance, impedance, or voltage. Since the breach could be small and intermittent as it starts, it can be difficult to detect as a flow but the cumulative gain or loss of the electrolytes from the contents or surrounding body fluids could cause a change in the resistance, capacitance, or impedance across the conductors. Alternatively, the detection circuit is closed and the contact of the contents or the body fluids with the conductors could cause a break, disruption, or change in the functioning of the circuit. In the exemplary embodiments described below, the conductors may comprise meshes, films, or other relatively large surface areas covering most or all of the wall so that breach at any point in the wall will provide the intended electrically conductive bridging between the conductors. The coupling of the conductors may also cause, alter, or enable a signal emission to alert the patient of the breach or potential breach. The spaced-apart conductors can have anyone of a variety of shapes or configurations, continuous configurations, such as plates and films, or discontinuous configurations, such as lattices, meshes, and the like, can be placed in various locations, preferably near interior portions of the device where body fluids will pool to enhance sensitivity and reliability of the detection.

Alternatively, the detection and signaling circuit may comprise at least two conductors coupled to a third conductor which is part of the functional circuitry or is embedded in the solid component of the device or is the solid component itself. In the event any of the conductors, and the third, functional conductor in particular, is fractured, even intermittently, a circuit is broken thereby causing a signal alteration by the signaling circuit to alert the patient of the breach or potential breach. The detecting conductors can have any one of a variety of shapes or configurations, including continuous configurations, such as plates and films, or discontinuous configurations, such as lattices, meshes, braids, fabrics, and the like, and can be placed in various locations, preferably spanning parts of the device where fractures are prone in order to enhance sensitivity and reliability of the detection. More than one of these couplings could be made in any configuration or location on a device to determine the site of the breach.

The signaling circuit can be active or passive. In a preferred embodiment, the signaling circuit will comprise a passive transponder and antenna which are adapted to be powered and interrogated by an external reader. Such transponder circuitry may conveniently be provided by using common radio frequency identification (RFID) circuitry where the transponder and tuned antenna are disposed on or within a protected area in the prosthesis and connected to remaining portions of the signaling circuit. Passively powered circuitry is particularly preferred in devices with on board batteries where the amount of energy stored in the battery generally determines the functional product life. The antenna and transponder could be located in close proximity to the detection circuitry or placed elsewhere in the device or another part of the body. For example, by connecting the transponder circuitry to "open" conductors which is closed in the presence of body fluids and/or inflation medium, the signal emitted by the transponder upon interrogation by an external reader may be altered. Thus, the patient or medical professional may interrogate the prosthesis and determine whether or not the prosthesis remains intact or the threat of an impending breach exists. This is a particularly preferred approach since it allows the user to determine that the transponder circuitry is functional even when a breach has not occurred.

The present invention further provides methods for signaling breach of a wall or covering of an inflatable prosthesis, electronic prosthesis, solid prosthesis, electrical cable, or the like. Usually, signaling comprises generating an emission by closing a signaling circuit when the wall or part of the device is at least partially breached. Usually a flow of electrolytes occurs when the wall or part of the device is at least partially breached, thereby closing the signaling circuit. To detect a near complete or complete fracture in solid components, generating an emission may comprise opening a signaling circuit when the wall, covering, or other part is substantially breached or generating an electrical current when the part is substantially breached. The particular signaling circuits and transmission modes have been described above in connection with the methods of the present invention.

The signaling system of the present invention can be designed to function using any one of a variety of algorithms to notify the patient in a simple, unequivocal fashion. For example, in a toggle algorithm, the transmitter is either on in the static state or preferably off in order to reduce the need for power. Upon direct contact between the conductors and the body fluids and or device contents, the now closed circuit cause the transmitter to turn the signal off or preferably on to be able to send a wireless signal on a continuous basis. The wireless signal or lack thereof depending on the algorithm is recognized by the detector to notify the patient that the integrity of the device is compromised.

Alternatively, the algorithm could be based on time, amplitude, frequency, or some other parameter. For example, the transmitter may send a wireless signal at a predetermined time interval in its static state. The detector recognizes the length of the interval as normal and the existence of the signal as the system in working order. Upon direct contact with the body fluids or device contents by the probes, the transmitter is enabled to send the same signal at different time intervals or a different signal, which is recognized by the detector to notify the patient that the integrity of the device is compromised. The lack of a signal is recognized by the detector to notify the patient of a detection system malfunction and potential compromise of the integrity of the device.

Optionally, more than one probe or more than one type of probe may be placed internally in different parts or components in the device so that the particular part or component which failed may be identified based on which probe was activated. The transmitter would send different signals for the receiver to display the source of the failure.

The internal probe could be of any shape and is disposed in the interior or preferably in the wall or covering of the device. The preferred configuration is a fine lattice or continuous film of the detection material embedded in the wall or in between layers of the wall covering the entire device, thereby conforming to the shape of the device. Such a configuration optimizes the performance of the system in detecting failures early. As the site of the tear or rupture cannot be predicted, the probe would be unlikely to miss detecting the breach by covering the entire device.

Compromise of the device typically starts with a somewhat linear split or tear in surface of the device wall or covering from mechanical fatigue or handling damage. As the split propagates, it will expose more and more lines of the lattice or area of the film to the body fluids and or device contents. Consequently, as the size and seriousness of the breach increases, the probability of detection increases. Embedding the detection material in the covering such as the wall of the balloon further enables detection before a full breach of the entire thickness of the device wall.

The detection material could be any metal, polymer, fiber, ingredient, or combination thereof, with or without any coating that can generate an electrical charge or enable flow of electric current when in contact with the body fluids or device contents. For example, an electrical charge could be generated from a non-toxic chemical reaction when the lattice exposed underneath a tear comes in contact with the body secretions. Flow of electric current could be enabled when two ends of an electric circuit hitherto physically separated by electrically non-conductive material in the covering or a structural element of the device are in contact with electrolytes in the body secretions when the electrically nonconductive material is compromised. For example, a charged lattice is embedded in the wall separated by silicone rubber from the ground probe on the external surface of the device. When the lattice is exposed to the electrolytes in the body fluids in the event of a tear, the circuit is closed. Alternatively, the lattice and ground could be separate from each other but interlaced in the wall of the device. Preferred materials include non-corrosive, biocompatible metals and elastomers, inks, or the like which contain electrically conductive particles.

The transmitter can be a simple wireless signal generator triggered by an electric current or preferably a transponder using the well-established RFID technology, i.e., produces a wireless signal when triggered by an interrogating signal. The electric charge generated or the electric current enabled by the probe in contact with the body fluids or device contents changes the logic state thereby enabling the transmitter to emit or causes it to emit a wireless signal. Typically, the transponder is powered by the interrogating radio frequency signal so that no power source of its own is required. Alternatively, the transmitter could be powered by a micro battery or by the electrical power generated by a chemical reaction. For protection from degradation by an acidic and electrolyte solution and become potentially toxic, the transmitter or transponder circuit is encased in a highly resistant material, such as silicone rubber or stainless steel. The transmitter or transponder circuit can be placed on the exterior, embedded in the wall, or preferably in the interior of the device for shielding from chemical degradation and mechanical stress. It can be placed in any orientation, preferably in the plane where the antenna is most sensitive and the transmitter is most effective in sending and receiving signals through body tissue overlying the device.

The wireless signal from the transmitter is recognized by a separate detector, typically external to the body. The detector could be simply a receiver tuned to the transmitter's signal or, preferably, a combination of both a transmitter of a signal to interrogate the transponder and a receiver to distinguish the different signals from the transponder. The detector is preferably powered by batteries and portable enough to be worn on a wristband, necklace, or belt or can be placed conveniently near a place where the patient spends most of his time. Upon receiving a signal that a breach has occurred, the detector will alert the patient to seek medical assistance or alert medical professionals directly through other devices, such as Bluetooth linked to an autodial telephone. The alarm could be auditory, such as beeping sounds, visual, such as flashing LED's or a LCD display, sensory, such as vibrations, or preferably a combination of any or all of the above.

Optionally, the detector could have different auditory, visual, sensory, or different combinations to identify the source of the detected breach, especially with more than one probe or more than one type of probe. For example, LED's of different colors or different sounds could be used. The alarm could further indicate the seriousness of the breach. For example, when multiple probes detect a breach, the volume of the alarm would increase to a higher level.

In the case of electronic implantable devices, such as pacemakers and defibrillators, the devices will be subject to failure due to intrusion of body fluids through breaches, particularly at the seams and lead connections. Thus, the detector circuit components described above could be located within the device canister near those seams and connectors at risk of failure so that initial penetration of fluids could be detected before sufficient amount of fluids, liquid or vapor, has entered to cause failure of the device.

In the case of electrical leads used in electronic stimulation devices, a breach in the insulation and a breach in the conductor can both be detected. The embodiments described above are particularly suitable for detecting a breach in the covering insulation from wear and tear. Usually this breach will precede and can serve as a sentry for a breach in the conductor. A breach in the conductor without a breach in the insulation can be detected by a closed circuit formed by two conducting probes, one coupled to the conductor near its proximal end and the other at its distal end. Any fracture or disruption of the current flow in the conductor, whether made of a metal, elastomer, or gel, between the two points will result in "opening" the circuit. An opening will change the logic state of the detection circuit and enable the transmitter to emit or causes it to emit a wireless signal. The detection and transmitting circuitry could be attached to any part of the lead or is in its own separate housing connected to the lead by the conducting probes. Thus, the detection and transmitting circuitry could be placed in a preferred orientation where normal body movements would not cause any sharp angles in the conductors and an area away from sites where wear and tear are more prone.

In the case where electrical leads are coupled to another conductor such as the connector outside the canister containing the functioning hardware and software, the principles and methods can detect detachment of the lead. In this embodiment, one probe is electrically coupled to the male and another probe to the female side of the connection. When the lead is detached from the connector, the circuit is thereby "opened" and detected as a breach.

In the case of solid devices, such as artificial joints or heart valves, the conductors are embedded in the device components prone to failure. The detection and transmitting circuitry could also be embedded in the device or placed in an area away from sites where wear and tear are more prone or signal transmission could be adversely affected.

In one aspect, the present disclosure provides improved gastric balloons and methods for their deployment and use. The balloons may have an overall volume or displacement selected to leave a residual volume in the proximal area of the stomach in the range from 10 ml to 100 ml, usually from 20 ml to 40 ml. As discussed in detail below in some embodiments, the volume may be adjustable to optimize treatment on individual patients. The gastric balloons may be designed to conform to the natural shape of the gastric cavity while maintaining the normal function of the stomach. The balloon may have a crescent or "kidney" shape to align the balloon wall against the greater and lesser curvatures of the stomach, an oval cross section to conform to the shape of the cavity in the sagittal plane, and delineate a space proximally for the collection of ingested food and another space distally for active digestion.

In one aspect, the gastric balloons include at least two principal structural components. The first principal structural component is an expandable scaffold which helps define a shape conforming to a gastric cavity, typically a crescent or "kidney" shape, when expanded. The scaffold may be self-expanding, e.g. formed from a shape memory metal or shape memory polymer, or may be inflatable with an incompressible fluid, such as saline, water, oil, gel, or other liquid, gel, slurry, solution, or the like. Use of an incompressible inflation or filling fluid can help rigidify the scaffold so that it maintains its shape for extended periods when implanted in the stomach. The expanded shape and side of the scaffold by itself or together with an intact portion of the device may form an object that is too large in all orientations, even when compressed in peristalsis, to permit the device to pass the pylorus.

The second principal structural component may include one or more inflatable or otherwise expandable space-occupying structures or compartments which are secured to the interior and/or exterior of the expandable scaffold. The space-filling structures or compartments assume a space-filling configuration when inflated or otherwise filled or expanded, typically being inflated or filled at least partly with a compressible fluid, typically a gas such as air. Such filling or inflation of the scaffold and/or the space-filling compartment(s) may be accomplished from an external pressurized fluid source, but certain gaseous inflation media can be generated in situ within the component by chemical reactions induced by mixing reactants or otherwise initiating a gas-producing chemical reaction. In some cases, the scaffold may form all or a portion of the space-filling structure or compartment.

The gastric balloons, as described herein, may comprise two or more walls or layers or lamina of materials to improve the durability of the device by optimizing the performance characteristics of different materials. This is desirable because the maximal thickness of the entire device in its deflated state such that it can be passed uneventfully through the esophagus is limited and is useful even for a simple, single compartment balloon. Typically, the outermost layer is made of materials, such as silicone rubber, selected primarily for their biocompatibility in the stomach and resistance to an acidic environment and the innermost layer is made of materials selected primarily for their resistance to structural fatigue and permeability to the filling fluid. In addition, use of multiple layers allows the layers to be formed from different materials having different properties, to enhance the performance characteristics of the entire balloon structure. The inner layers could have biocompatibility of a shorter duration than the outermost layer. It may be desirable to enhance the durability further by embedding other structural elements in the layers, such as a mesh made of metal, polymer, or high strength fibers, such as Kevlar®. In the simplest embodiment, the two layers are either bonded together to function as a single wall or left unbonded such that the layers could slide by each other except at certain attachment points.

Optionally, a variety of structural elements may reside in between the outermost and innermost layers. For support, the mesh of high strength fibers, polymer, or metal could constitute another layer in of itself instead of being embedded in the layers. Alternatively, the mesh forms or is a component of the expandable scaffold. One or more layers of materials selected for the optimal balance of biocompatibility, impermeability, rigidity, durability among other criteria could be added to enhance the structural performance characteristics of the device further.

The inflatable compartment(s) may be inflated with compressible fluids (gases), incompressible fluids (liquids), or in some cases mixtures of gases and liquids. When multiple inflatable compartments are used, each compartment may be inflated with the same or different gas(es), liquid(s), and/or mixtures thereof. The use of gas and liquid for gastric balloon inflation has a number of advantages. A principal benefit is the ability to control buoyancy and weight distribution within the balloon, e.g., by filling most of the compartments with a gas and distributing the non-gas inflation medium in other compartments throughout the balloon, the risk of concentrated pressure points against the stomach is reduced. Second, by properly controlling the ratio of air or other gas to saline or other liquid, the gastric balloon can be provided with a desired buoyancy and mass within the stomach. Typically, the ratio of air:liquid can be in the range from 2:1 to 10:1, more preferably within the range from 3:1 to 6:1. Such ratios can provide effective densities relative to water at a specific gravity in the range from 0.09 to 0.5, usually from 0.17 to 0.33, depending on the total volume occupied by the device. Typically, the weight of the filled balloon is in the range from 50 gm to 500 gm, usually being from 50 gm to 450 gm. The use of gastric balloons which are light and less dense will reduce the risk that the balloons will cause abrasion, pressure induced lesions, shearing lesions, or other trauma when implanted in the stomach for extended periods of time.

Optionally, gastric balloons may include at least one separately inflatable or otherwise expandable external bladder formed over an exterior surface of the balloon. The external bladder(s) can be separately inflatable from both the scaffold and the space-filling compartment(s) although they may be attached to or share common walls with either or both of these other principal structural components. The bladder may be positioned on the exterior of the balloon so that it can control either or both of the shape and buoyancy of the balloon as a whole. Typically, the bladder will be inflated at least partly with a compressible gas, typically air or other biocompatible gas. Often, the balloon will be underfilled, i.e., filled with a volume that does not distend or increase the wall tension beyond that of the unfilled bladder.

The expandable scaffold, the inflatable space-filling compartment(s) or structures, and optionally the inflatable bladder(s) may be joined together in the overall gastric balloon structure in a variety of ways. Typically, each component may be separately formed and joined by adhesives, bonding, or by other non-penetrating fasteners, or by other means. Alternatively, all or a portion of these principal structural components may be formed by co-extrusion to provide the desired inflatable volumes.

The external bladder(s) may also be formed from elastic and/or inelastic materials, such as silicone rubber and polyethylene terephthalate film (Mylar®), respectively, so that they can be inflated at the end of the procedure to properly position the gastric balloon within the stomach and to provide for proper sizing of the balloon within the stomach. In an illustrated embodiment, the gastric balloon includes one space-filling compartment and one external bladder for each of the four channels formed by the inflatable scaffold, but the number of compartments and/or bladders may differ from the number of channels.

Some embodiments include at least two or more inflatable-space-filling compartments and in some cases may also include one or more inflatable external bladders. The inflation of multiple inflatable compartments and external bladders may be accomplished in a variety of ways. Most simply, each inflatable compartment and inflatable external bladder (if any) could be connected to an independent inflation tube which can be disconnected after inflation. The use of multiple independent inflation tubes allows each inflatable compartment and external bladder to be selectively and independently filled, further allowing filling at different pressures, with different inflation fluids, and the like. The use of multiple inflation tubes, however, is not generally preferred since the tubes, collectively, can have rather a large cross section, and such multiple tubes may interfere with device deployment.

The multiple inflatable compartments and external bladders of certain embodiments may be filled through a single inflation tube in at least two ways. First, by connecting the inflatable compartments and external bladders in series, for example using a series of one-way valves, inflation through a first inflatable compartment (or external bladder) can sequentially fill additional compartments and bladders in the series as the pressure in each compartment raises and in turn begins to fill the next compartment or bladder in series.

In one aspect, a selective valve system can be accessed and controlled by a single inflation tube in order to independently and selectively inflate each of the inflatable compartments and external bladders (if any). Such selective valving system may be constructed in any of at least several ways. For example, an inflation tube having a lateral inflation port near its distal end can be disposed between two, three, or more one-way valves opening into respective inflatable compartments and external bladders. By rotating the inflation tube, the inflation port on the tube can be aligned with one of the one-way valves at a time, thus permitting inflation of the respective compartment or bladder to a desired pressure and with a desired inflation fluid, including liquid inflation fluids, gaseous inflation fluids, and mixtures thereof. The rotatable and selectable inflation tube could be removable. Alternatively, at least a portion of the inflation tube could be permanently mounted within the gastric balloon structure, allowing an external portion of the inflation tube to be removably coupled to the internal portion to deliver the inflation fluids.

In addition to rotatably selectable inflation tubes, the inflation tube could be axially positionable to access linearly spaced-apart one-way valve structures, each of which is connected to a different inflatable compartment or external bladder.

As a still further alternative, a single inflation tube could be rotatably mounted and have several inflation ports along its lengths. Each of the inflation ports could be disposed near one, two, or more different one-way valves communicating with different inflatable compartments and/or external bladders.

The one-way valves may permit inflation by introducing an inflation medium at a pressure sufficiently high to open the one-way valve and permit flow into the associated inflatable compartment or external bladder. Upon removing the pressurized inflation source, the one-way valve closes and remains sealed in response to the increased pressure within the inflatable compartment or external bladder.

The inflation tube(s) may be removable from the connected component after the component or multiple components have been inflated. Thus, as described in more detail below, the gastric balloon may be delivered to the stomach in a deflated, low profile configuration, typically through a gastroscope or other transesophageal delivery device. Once in place, the inflatable components may be inflated, filled, or otherwise expanded in situ to a desired volume and buoyancy typically by delivering the inflation media through the inflation tubes.

Once the desired inflation size is reached, the inflation tubes may be detached from each of the compartments allowing self-sealing so that the inflation medium remains contained for extended periods of time. To ensure the containment of the medium, valves may be placed in series for any one or more of the inflatable component(s) and/or bladder(s). Other expansion protocols are described elsewhere herein. In particular, component, compartment, or portion of the balloon may be inflated in situ by inducing a gas-generating reduction within the balloon. The reactant(s) may be present in the balloon prior to introduction to the patient or may be introduced using the connecting tubes after introduction to the stomach.

Although one illustrated embodiment includes four channels in the inflatable scaffold, it will be appreciated that the present disclosure covers gastric balloon structures having only a single passage or channel formed within the scaffold with a single space-filling compartment and single external bladder. Embodiments with two channels, space-filling compartments and external bladders as well as three channels, three space-filling compartments, and three external bladders, as well as even higher numbers will also be within the scope of the present specification.

The dimensions of the scaffold, space-filling compartment(s) or structure(s), external bladder(s), and/or isolated inflation chambers within any or all of these components, may be selected such that the collective volume or physical dimensions of the chambers remaining inflated after deflation of any single chamber (or limited number of chambers) is sufficient to prevent passage of the balloon through the pyloric valve. Usually, the volume(s) will be such that at least two inflatable components and/or chambers within said components could deflate without risk of the "diminished" balloon passing through the pyloric valve, preferably at least three could deflate, and often at least four or more chambers could deflate. The precise volume(s) necessary to prevent passage of the partially deflated balloon structure through the pyloric valve and may vary from individual to individual. A preferred remaining residual inflated volume may be at least about 75 ml, preferably at least about 100 ml and still more preferably at least about 200 ml. After partial deflation, the balloon should have a dimension along any axis or its cross axis of at least 2 cm, preferably at least 4 cm, and most preferably at least 5 cm.

In one aspect, the present specification relates to methods for treating obesity in a patient. The methods may comprise introducing a gastric balloon structure to the patient's stomach. An inflatable scaffold which forms part of the balloon may be filled with an incompressible fluid to provide a fixed support geometry. At least a portion of a separate space-filling compartment may be filled at least partly with a compressible fluid, typically a gas such as air, nitrogen, or the like, within the remainder (if any) being filled with an incompressible material, such as a liquid, gel, slurry, or the like. In this way, the buoyancy of the balloon may be controlled within the limits described above.

The methods of the present specification may include determining the size of the gastric cavity and selecting a gastric balloon of proper size prior to introducing the balloon to the stomach. Such size determination may comprise visually examining the gastric cavity, typically under direct observation using a gastroscope, but alternatively using fluoroscopy, ultrasound, x-ray or CAT scanning, or any other available imaging method. An estimate of the dimensions of the stomach and the size of the device can be made by direct observation of the interior of the stomach immediately prior to deployment. Alternatively, the dimensions of the feeding stomach, which is generally larger than the resting stomach, and the size of the device will be determined at an earlier session where the patient has consumed or swallowed a biocompatible filling medium, e.g., water, contrast medium, food, etc. A sufficient amount of filling medium will be consumed so that the imaging technique can detect full relaxation of the stomach during feeding and estimate its dimensions and size.

Introducing may include passing the gastric balloon in a deflated configuration into the stomach through the same gastroscope. Alternatively, the deflated balloon could be introduced into the gastric cavity via an attachment to an orogastric or nasogastric tube. The balloon may be oriented so that the scaffold will open with curved geometry conforming to the curve of the gastric cavity. The scaffold may be released from constraint to self-expand or will be filled through a removable inflation tube attached to the scaffold, where the inflation tube may be removed after filling. The scaffold may then be sealed or be self-sealing upon detachment of the filling tube(s) to prevent loss of the inflating liquid medium. Similarly, the space-filling compartment(s) may also be filled through one or more inflation tube(s) removably attached to the compartment(s), where the tube(s) are removed after the compartment(s) have been filled with the desired medium, for example a mixture of liquid and gas sources. Further, the external bladder(s) may be filled through one or more inflation tube(s) generally as described above for both the scaffold and the space-filling compartment(s).

After all the principal structural components of the gastric balloon have been inflated or otherwise expanded and the associated inflation tubes released, any other anchors or tethers attached to the balloon may also be released, leaving the balloon free to "float" within the patient's stomach. By properly selecting the ratio of liquid inflation medium to gas inflation medium, as discussed above, the weight, distribution, and the buoyancy of the gastric balloon may be such that the balloon rests within the stomach without exerting undue pressure at any particular point, thus reducing the risk of abrasions or other trauma to the stomach lining. The inflated gastric balloon may be left in place for extended periods of time, typically as long as weeks, months, or even years.

After the balloon has been inflated and left in place, it may become desirable to adjust the size and/or buoyancy of the balloon for purposes of patient comfort, efficacy, or other reasons. To perform such adjustments, the balloon may be transesophageally accessed, typically using a gastroscope with suitable working tools introduced therethrough. For example, the balloon may be grasped with graspers and inflation tubes may be suitably attached or docked to inflation ports on the balloon structure. For example, the inflation ports may be located near the end of the gastric balloon structure which is oriented toward the top of the stomach so that they are readily accessed through the gastroscope. After attachment with the inflation tube, the inflation medium can be introduced and/or extracted, depending on whether the particular structural component is to be enlarged, deflated, or have a buoyancy adjustment. Optionally, an incising instrument could be introduced through the gastroscope to penetrate and deflate any filled compartment to reduce the overall volume of the device and improve accommodation of the device. Typically, these compartments are small to allow minor adjustments without jeopardizing the integrity of the device itself.

In addition to adjusting the size and/or buoyancy of the gastric balloon, it may become desirable or necessary to remove the balloon completely. To effect such removal, the balloon may be accessed transesophageally, typically using a gastroscope. The balloon may first be grasped or secured using a grasping tool. Then, one or more surfaces of the balloon may be penetrated or breached in order to release the contents of the balloon into the stomach. The contents may be biocompatible gasses or liquids so that release into the stomach will not be a concern. After the contents of the compartments have been released, the balloon may then be pulled through the patient's esophagus, for example by pulling with the grasping tool. It may be possible to pull the deflated gastric balloon through the working channel of the gastroscope, but more often the balloon will simply be withdrawn through the esophagus as the gastroscope is withdrawn. Optionally, a sheath or other protective cover may be placed over the deflated balloon in order to reduce the risk of trauma or injury to the esophagus upon withdrawal.

BRIEF DESCRIPTION OF THE DRAWINGS

FIG. 15D is a cross-sectional view taken along line 15D-15D of FIG. 15C.

FIG. 15E illustrates an example gastric balloon including a pair of inflatable space-filling compartments contained by an external sheath.

FIG. 15F illustrates an example gastric balloon having two inflatable space-filling compartments joined together by a spine structure.

DETAILED DESCRIPTION OF THE INVENTION

Figure 1:
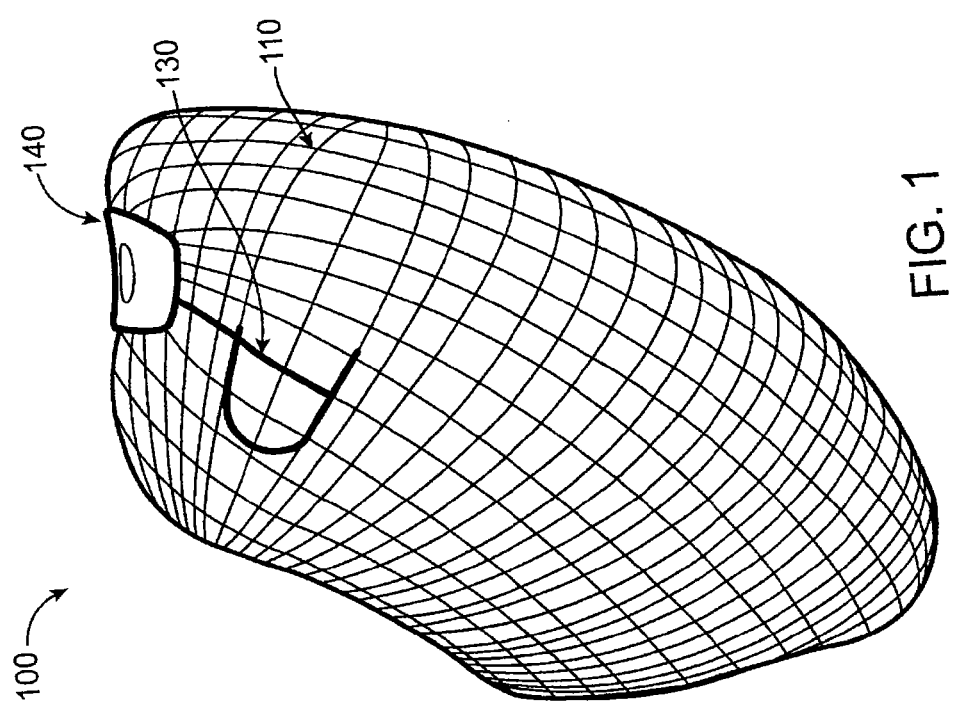
FIG. 1 illustrates a gastric balloon having the wall breach detections system of the present invention incorporated therein.

Referring now to FIG. 1, the gastric balloon 100 includes two electric probes. Probe 130 is on the external surface in contact with the surrounding tissues, body fluids, and contents of the stomach. Probes 130 and 110 can have any of a variety of shapes or configurations, including circular plates, lattices, films, and the like, cover all or a portion of the balloon or other device. Probe 110, shown here in a lattice configuration, provides the second probe incorporated in the wall of the balloon. The probe material could be any metal, polymer, fiber, or combination thereof, with or without any coating that can generate an electrical charge or enable flow of electric current when in contact with the stomach contents. The probes are connected electronically to the wireless transmitter 140, but are separated from each other by at least one layer of non-conductive material in the balloon wall. The transmitter can be a simple wireless signal generator triggered by an electric current or preferably is an unpowered transponder using well-established RFID technology which produces a wireless signal in response to an interrogating signal. In the intact state when the wall is not breached, components 130, 110, and 140 comprise an open electrical circuit and the transmitter is inactive, disabled, or enabled to transmit a base signal.

Figure 2:
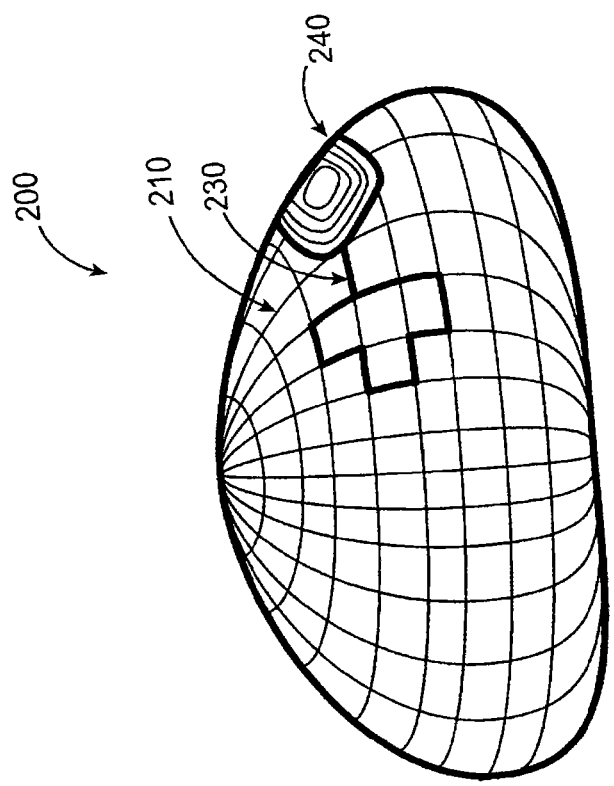
FIG. 2 illustrates a breast implant having the wall breach detection system of the present invention incorporated therein.

Referring now to FIG. 2, a breast implant 200 may be similarly formed with a lattice 210 formed within the breast wall, an external electrically conductive probe 230 formed on or over the exterior surface of the implant, and a transmitter 240 connected to both the lattice and exterior probe. In the case of breast implants filled with low conductivity materials, such as silicone gel, it may be desirable to provide conductive materials to enhance conductivity upon leakage.

Figure 3:
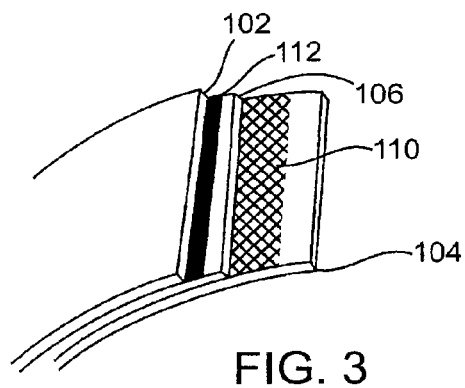
FIG. 3 illustrates a multi-layer wall structure useful for the prostheses of the present invention.

As magnified in FIG. 3, the second internal probe comprises both a fine lattice 110 and a thin film configuration 112 in the wall of the balloon in between, at the minimum two layers, an outermost layer 102 and innermost layer 104. The second internal probe can be also disposed in any enclosed space in the device (not shown). In the configuration described in FIG. 1, probes 130 and 110 and transponder 140 represent one open circuit and probes 130 and 112 and transponder 140 represent a second open circuit. Each open circuit is available to power or enable the transmitter or may enable the transponder to alter a base signal.

After the balloon is deployed in the stomach, the external probe 130 is in contact with the surrounding tissue and body fluids and stomach contents. Upon a breach in the integrity of the wall, such as a tear in the outermost layer 102, the leakage of physiologic fluid or stomach contents with electrolytes into the tear forms a salt bridge that closes the circuit formed probes 130 and 112 and transponder 140. Once the circuit is closed, a toggle is switched in the transponder, which will be enabled to transmit a "layer 102 breach" signal. Tears through layer 106 in the balloon wall will allow leakage of physiologic fluid or stomach contents with electrolytes into the tear forming a salt bridge that closes the circuit formed probes 130 and 110 and transmitter 140. Closing this circuit switches another toggle in the transponder, which will be enabled to transmit a "layer 106 breach" signal.

Figure 4:
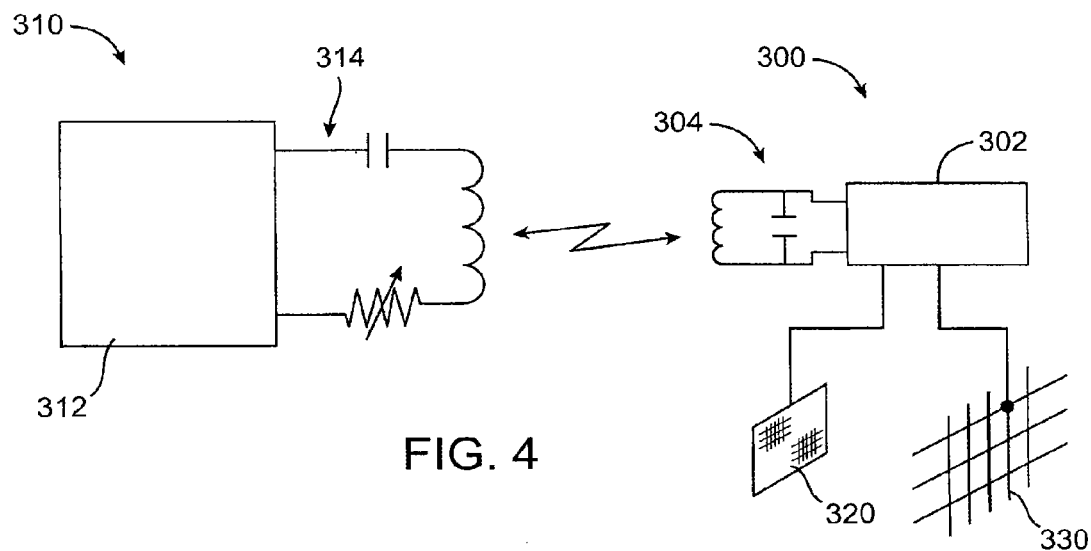
FIG. 4 illustrates a passive transponder system which may be utilized in the wall breach detection systems of the present invention.

The preferred radiofrequency identification circuit is shown schematically in FIG. 4. The circuit comprises a transmitter component 300 which includes transponder circuitry 302, typically formed as an integrated circuit, and a tuned antenna-capacitor circuit 304. An interrogator reader 310 comprises circuitry 312 including the power supply (typically a battery) demodulator circuitry, decoder circuitry, and the like. An antenna 314 is tuned so that it can communicate wirelessly with the antenna 304 of the transponder 300. Operation of this circuitry is generally conventional and provides for energizing, demodulating, and decoding signals between the external and implanted components. The transponder circuitry, however, will be modified so that the conductive elements implanted in the wall, such as film 320 and lattice 330 may enable or alter the signal emitted by the transponder when the conductive elements are bridged by body fluids or inflation medium. In the preferred embodiments described above, electrical coupling of the conductors 320 and 330 will alter the signal that is produced by the transponder 302. In that way, the patient or other user will be able to interrogate the transponder and receive a base or "normal" response signal when no wall breach has occurred. In the event of a wall breach, the signal emitted by the transponder will be altered so that the breach will be made evident.

Figure 5:
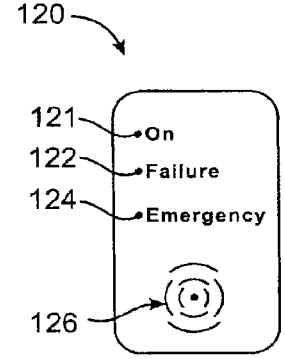
FIG. 5 illustrates a hand-held interrogation unit useful with the systems of the present invention.

An exemplary reader module 120 is shown in FIG. 5 and includes LEDs to indicate normal or "on" function, failure, and emergency failure. An audible the alarm 126 could also be provided to alert with beeping sounds, or sensory, such as vibrations, or preferably a combination of any or all of the above. Optionally, the detector could have different auditory, visual, sensory, or different combinations to identify the source of the detected breach, especially with more than one chemical substance used. The alarm could further indicate the seriousness of the breach. For example, when breaches are detected, the volume of the alarm would increase to a higher level.

Figure 6A:
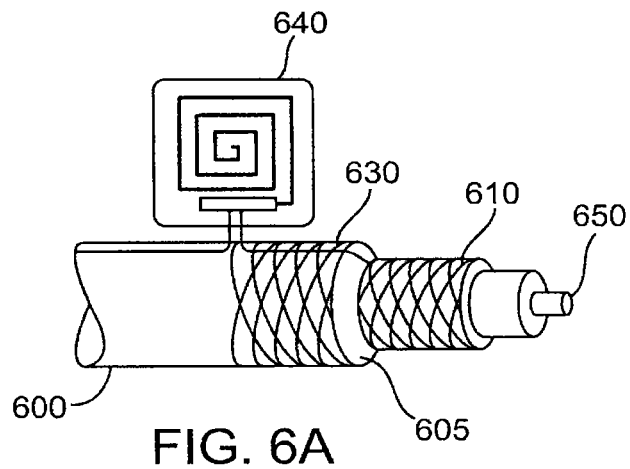
FIGS. 6A through 6I illustrate leads and connectors used in electronic stimulators having the covering breach detection system of the present invention incorporated therein.
Figure 6B:
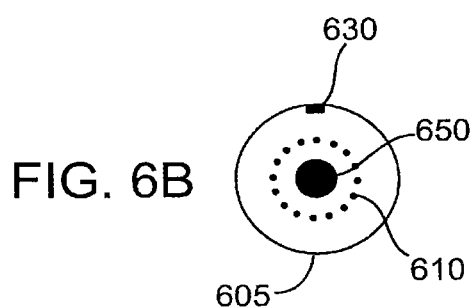
Figure 6C:
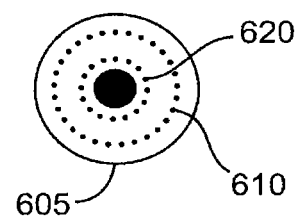
Figure 6D:
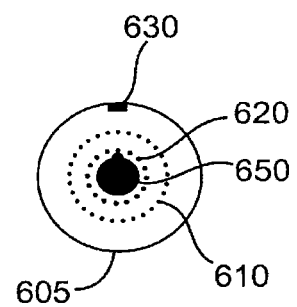
Figure 6E:
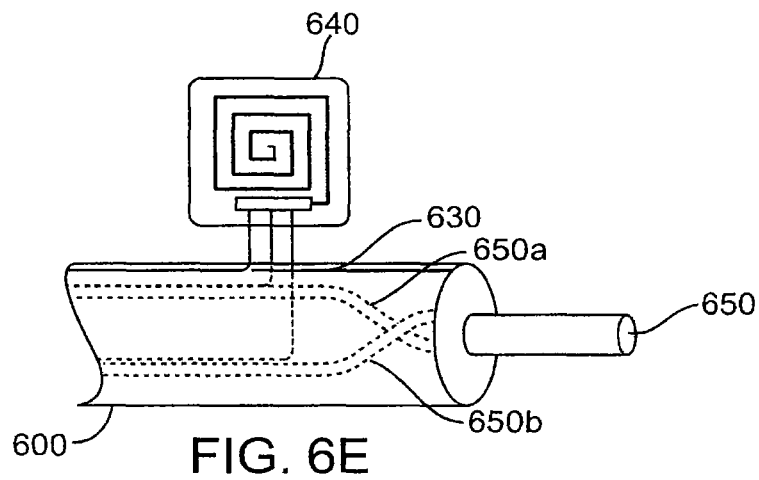
Figure 6F:
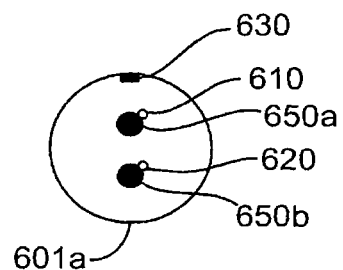

Referring now to FIG. 6A, an electrical lead 600 with a functional conductor 650 which is useful for cardiac or neuro stimulators may be similarly formed with an electrically conductive lattice 610 embedded within an insulating covering 605, an external electrically conductive cable coil 630 attached to the exterior surface of the implant, and a transmitter 640 connected to both the lattice 610 and external coil 630. As shown in the cross section FIG. 6B, the lattice 610 is preferably formed coaxial to the conductor 650 and separated from the conductor and the surrounding environment by inner and outer annular portions of the cover 605. The cross section of FIG. 6C shows conductive probes 610 and 620 in lattice form both embedded in the covering. The cross section of FIG. 6D shows a plurality of conducting probes 610 and 620 which are embedded coaxially in the insulating covering 605. In this embodiment, a current flow enabled by electrolytes between external probe 630 and 610 or 620 or the functional conductor 650 could indicate the extent of the breach. An alternative configuration is shown as lead 601 in FIG. 6E and FIG. 6F with two functional conductors 650a and 650b connected at their ends but electrically isolated from each other along their length so that each can serve as a backup for the other. In this configuration, the probes 610 and 620 do not have to be separated from but are in contact with the functional conductors.

Figure 6G:
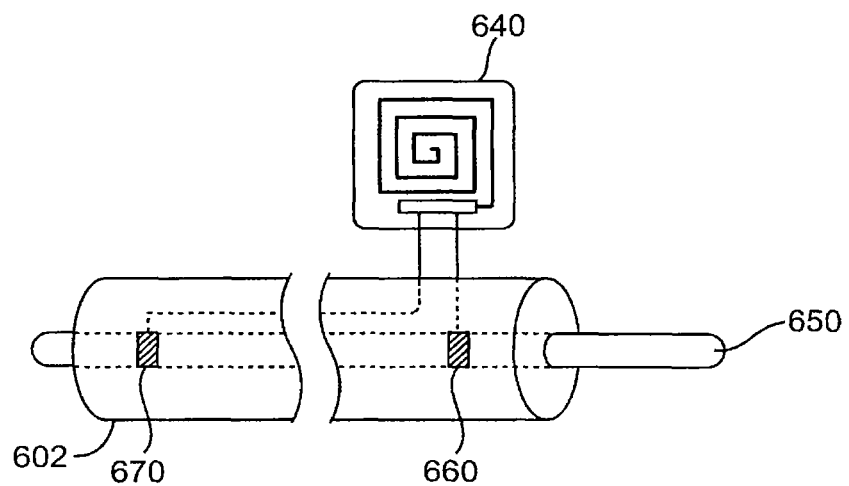

In the case of detecting a breach of the functional conductor, a lead 602 is shown with two electrically conductive probes 660 and 670 coupled to two ends of the functional conductor 650, as shown in FIG. 6G.

Figure 6H:
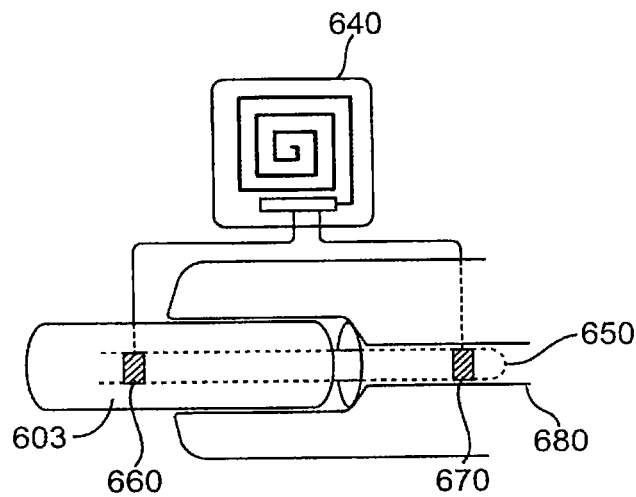
Figure 6I:
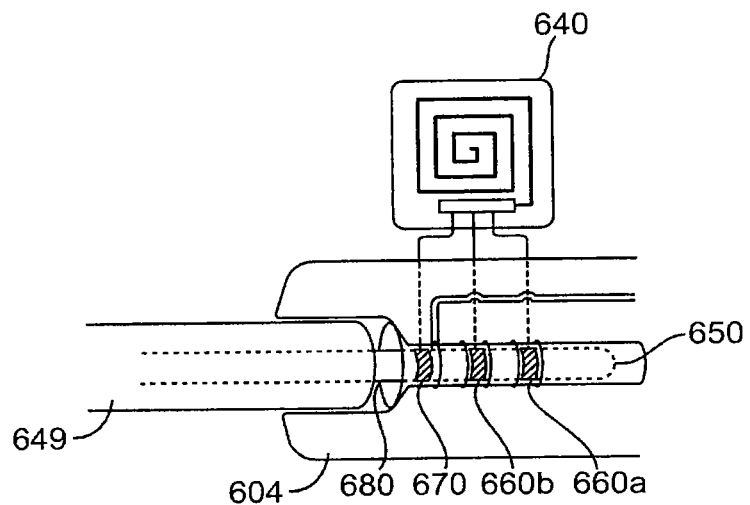

In the case where the functional conductor 650 is connected to another functional electrical conductor 680, as shown in FIG. 6H, a lead 603 is shown with a transmitter 640 with two probes, 660 and 670. Probe 660 is coupled to the functional conductor 650 and 670 to the other functional conductor 680, in this embodiment an electrical connector. One or both of the probes 660 and 670 are attached after the connection is made. Both probes 660 and 670 can be embedded in the functional conductor connection housing in either the male or female side, as shown in FIG. 6I. In this embodiment of a female connector 604, functional conductor 650 passes through and is electrically coupled to functional conductor 680. In this embodiment as electrically isolated rings inside the female connector 604, probe 670 is coupled to 680 and probes 660a and 660b coupled to 650. Such a configuration would enable detection of a partial detachment of the male member 649 when the circuit between 670 and 660b is closed but that between 660a and 660b is open and a possible complete lead detachment when all the detection circuits are open. The placement and physical length of the probes 660a and 660b would determine the amount of detachment necessary to open the circuit and enable the system to signal a breach.

While the leads and connectors incorporating the detection system are illustrated independently above, they may be configured independent to each other in a device system or together in any combination using one or more common detecting or signaling circuits.

Figure 7:
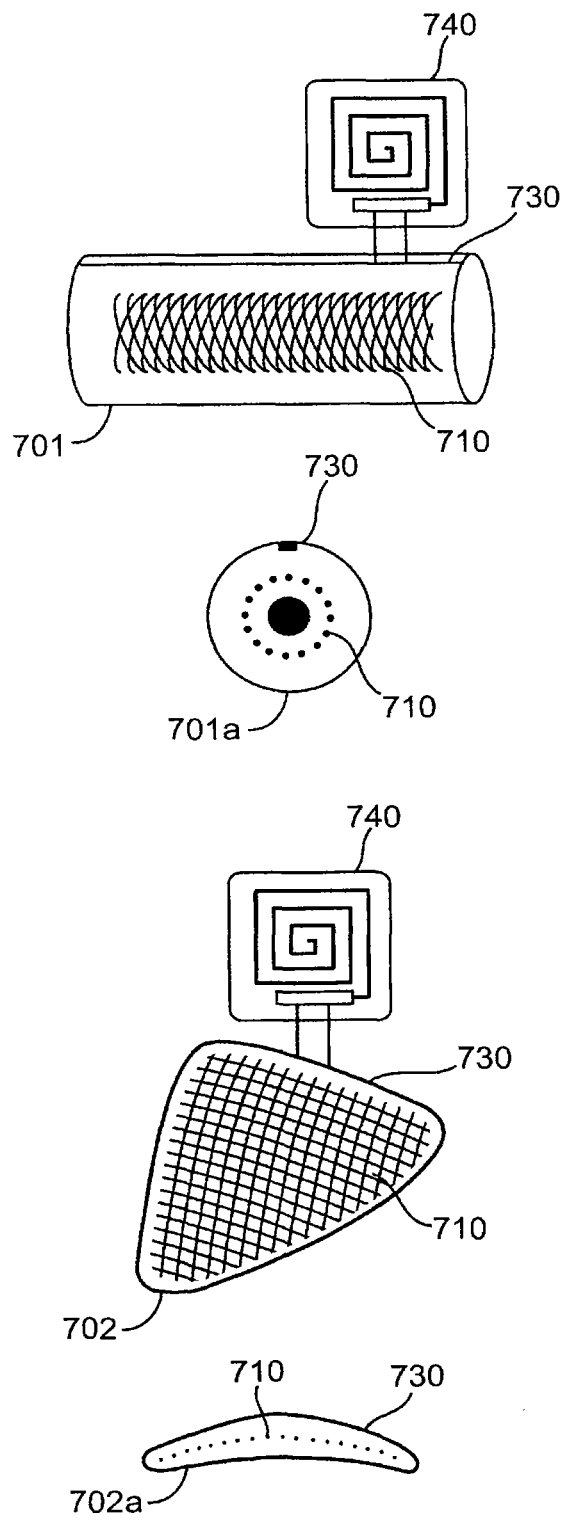
FIG. 7 illustrates solid device components having the wall breach detection system of the present invention incorporated therein.

Referring now to FIG. 7, two solid prosthetic device forms are shown. Cylindrical shaped 701 and a flat triangular shaped 702 are shown with a transmitter 740, an electrically conductive lattice 710, and an external electrically conductive probe 730. 701a and 702a are cross sections of each respectively. Any wear and tear or fracture deep to the lattice 710 is detected as a breach. It can be appreciated that the principle can be applied to a solid object of any shape. In the case of an object holding other parts of the device in place or within a range of motion (not shown), such as functioning like a ligamentous or cartilaginous structure in the body, respectively, detecting a breach of the object would indicate a potential dislocation of the other parts.

Figure 8:
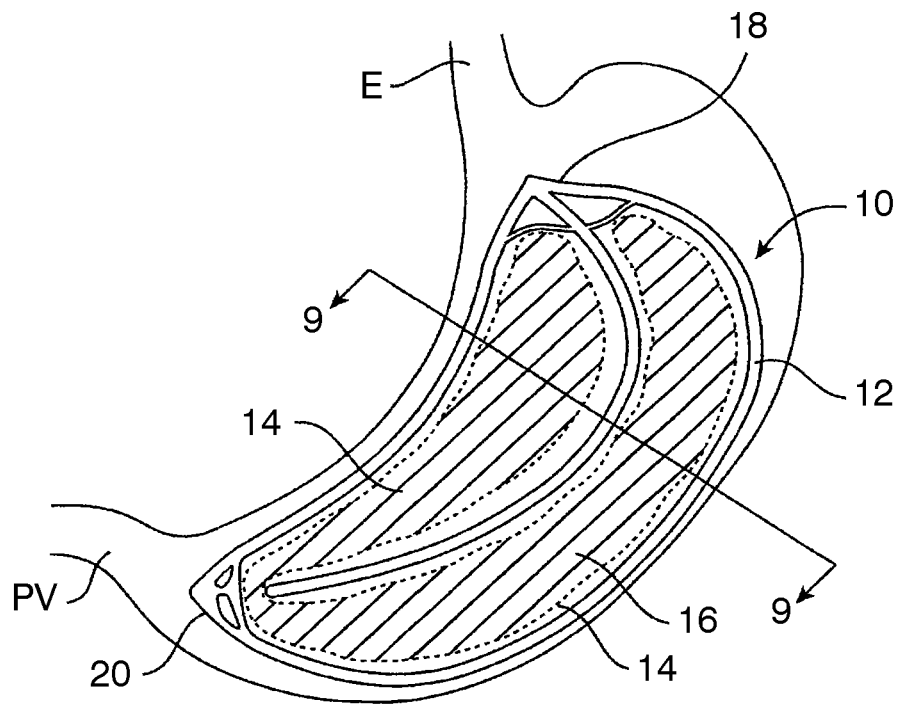
FIG. 8 is a side view of an example gastric balloon, shown deployed in a stomach.
Figure 9:
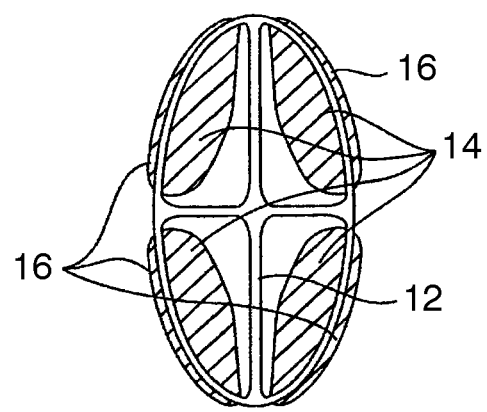
FIG. 9 is a cross-sectional view taken along line 9-9 in FIG. 8.

Referring now to FIGS. 8 and 9, a gastric balloon 10, in some embodiments, comprises an inflatable scaffold structure 12, four inflatable space-filling compartments 14, and four inflatable external bladders 16. Referring in particular to FIG. 9, the inflatable scaffold 12 has a X-shaped cross-section and defines four generally axially oriented channels or quadrants, each of which receives one of the four inflatable space-filling compartments 14. The four inflatable external bladders 16 are mounted over the inflatable space-filling compartments 14, and the balloon 10 includes an upper cage 18 and lower cage structure 20 which permit grasping of the balloon using grasping tools, as will be described in more detail below. In its deployed configuration, the gastric balloon 10 has a crescent or curved shape which conforms to the interior shape of a gastric cavity, with the upper cage structure 18 oriented toward the esophagus E, the lower cage structure 20 oriented toward the pyloric valve PV.

Figure 10:
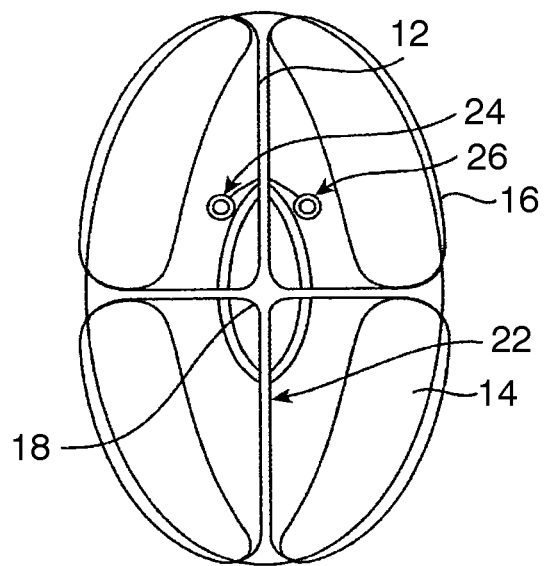
FIG. 10 is a top view of the gastric balloon of FIG. 8, illustrating the inflation ports or nipples.

Referring now to FIG. 10, the inflatable scaffold structure 12 is provided with at least one inflation port or nipple 22 while the inflatable space-filling compartments 14 are provided with a separate port 24 and the inflatable external bladders are provided with a separate inflation port 26. Although not illustrated, the scaffold, internal components, and external bladders could have isolated, inflatable volumes therein, each of which would be attached to a separate inflation tube. By "subdividing" the volume of the various principal structural components, the risk of accidental deflation of the balloon is further reduced.

Figure 11A:
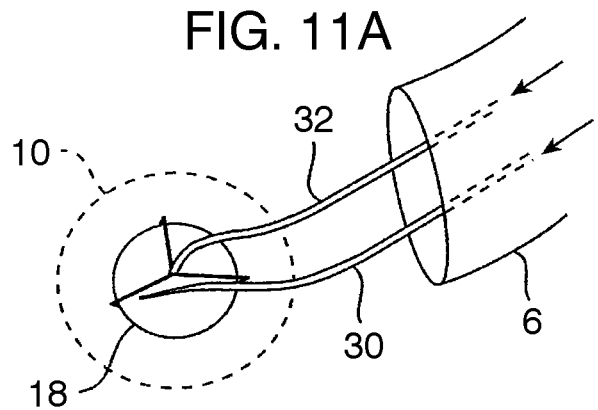
FIGS. 11A and 11B illustrate use of example tools introduced through a gastroscope for inflating and deflating a gastric balloon, respectively.

As illustrated in 11A, after the gastric balloon 10 is introduced in its deflated configuration into the gastric cavity, the inflatable structural components could be inflated using a single inflation tube 30 introduced through the gastroscope G, or orogastrically or nasogastrically by itself or using an orogastric or nasogastric tube. For example, the upper cage 18 can be held by a grasper 32 which can selectively hold and release the gastric balloon 12 during inflation and subsequent deployment. Shown in FIG. 11A, inflation tube 30 can be selectively coupled to any one of the inflation ports 22, 24, or 26, and the desired inflation medium introduced therethrough. Inflation tube 30 will be suitable for delivering either liquid or gas inflation media, typically including saline, water, contrast medium, gels, slurries, air, nitrogen, and the like.

In some embodiments, the inflatable scaffold structure 12 will be inflated entirely with a liquid or other incompressible medium, such as a gel, slurry, or the like. In contrast, the inflatable space-filling compartments 14 may at least partly be inflated with air or other gas. Often, however, the inflatable space-filling compartments will inflated with a mixture of gas and liquid in order to control the buoyancy of the balloon 12. Finally, the external bladders 16 may be inflated with gas in order to provide a relatively soft outer surface which can reduce trauma and abrasion.

The various structural compartments of the balloon may be made from the same or different materials. In some embodiments, the inflatable scaffold structure 12 will be formed from a non-distensible (non-stretching) material so that it may be inflated to become a relatively rigid structure. Alternatively, or additionally, the structures may be formed from stiffer materials and/or be reinforced to increase the rigidity when inflated.

In contrast, the inflatable space-filling compartments 14 and the inflatable bladders 16 may be formed in whole or in part from softer elastomeric materials in order to allow inflation flexibility, both in terms of size and density of the combined inflation media. The elastic nature of the external bladders allows the peripheral dimensions of the gastric balloon to be adjusted over a significant range by merely controlling inflation volume. Elastic inflatable space-filling compartments can allow the amount of space occupied in the interior of the balloon to be adjusted, for example to adjust the amount of volume filled by the balloons within the quadrants defined by the scaffold structure 12. Alternatively, the volume of incompressible fluid introduced into nonelastic structures may be sufficient to control the volume being occupied.

As an alternative to using a single inflation tube, each of the inflation ports 22, 24, and 26 could be pre-attached to separate inflation tubes. In such cases, after inflation of each structural component is completed, the necessary inflation tube could then be withdrawn through the gastroscope G, leaving the gastric balloon 10 in place.

Figure 11B:
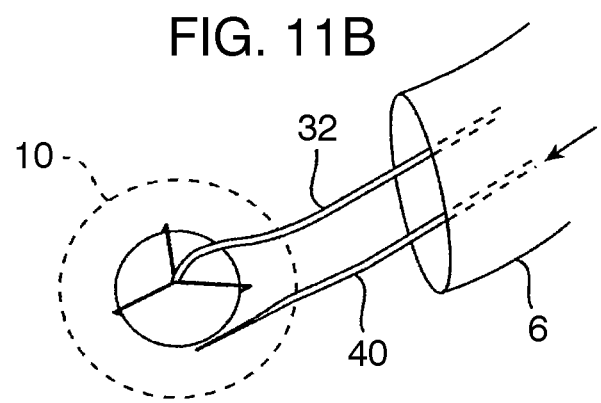

Referring now to FIG. 11B, the balloon 10 can be deflated while grasping the tip 18 of the balloon with grasper 32 through gastroscope G using a blade structure 40 introduced through the gastroscope. The blade structure 40 may be used to make one or more penetrations or breaches within each of the inflatable components of the gastric balloon, including the inflatable scaffold, the inflatable space-filling compartment(s), and the inflatable external bladder(s)

Figure 12A:
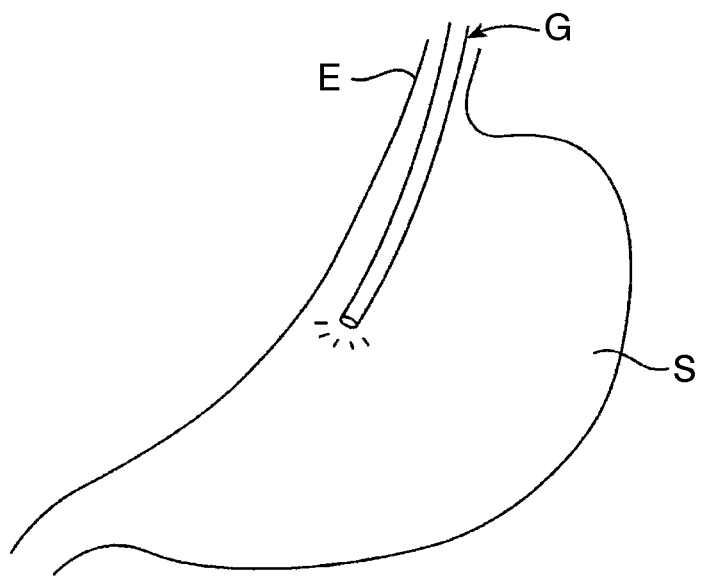
FIGS. 12A through 12E illustrate a complete deployment protocol according to example methods described herein.
Figure 12B:
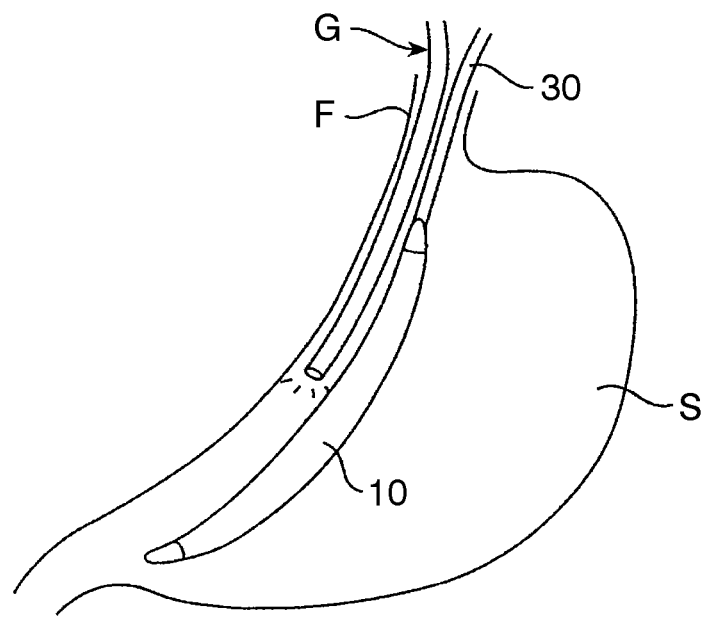

Referring now to FIGS. 12A-5E, gastric balloon 10 may be introduced to a patient's stomach S using a gastroscope G introduced through the esophagus E in a conventional manner. Standard procedures for preparing and introducing the gastroscope are employed, including checking for ulcerations in the esophagus and performing further examination if warranted.

Figure 12C:
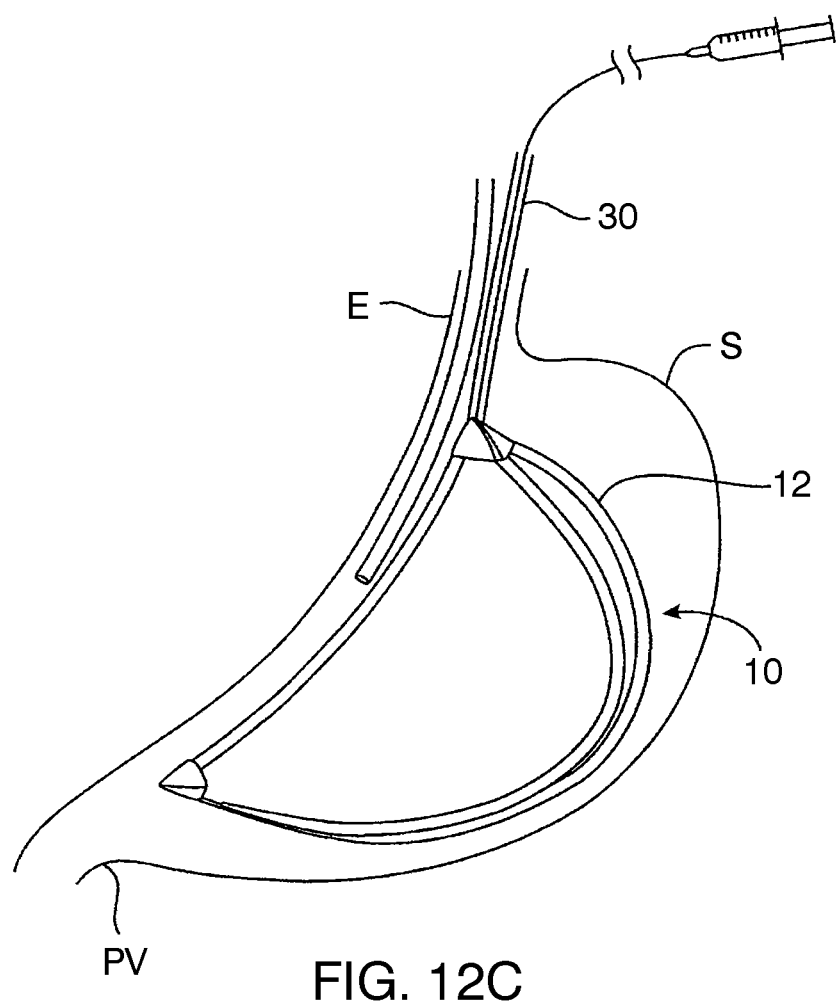
Figure 12D:
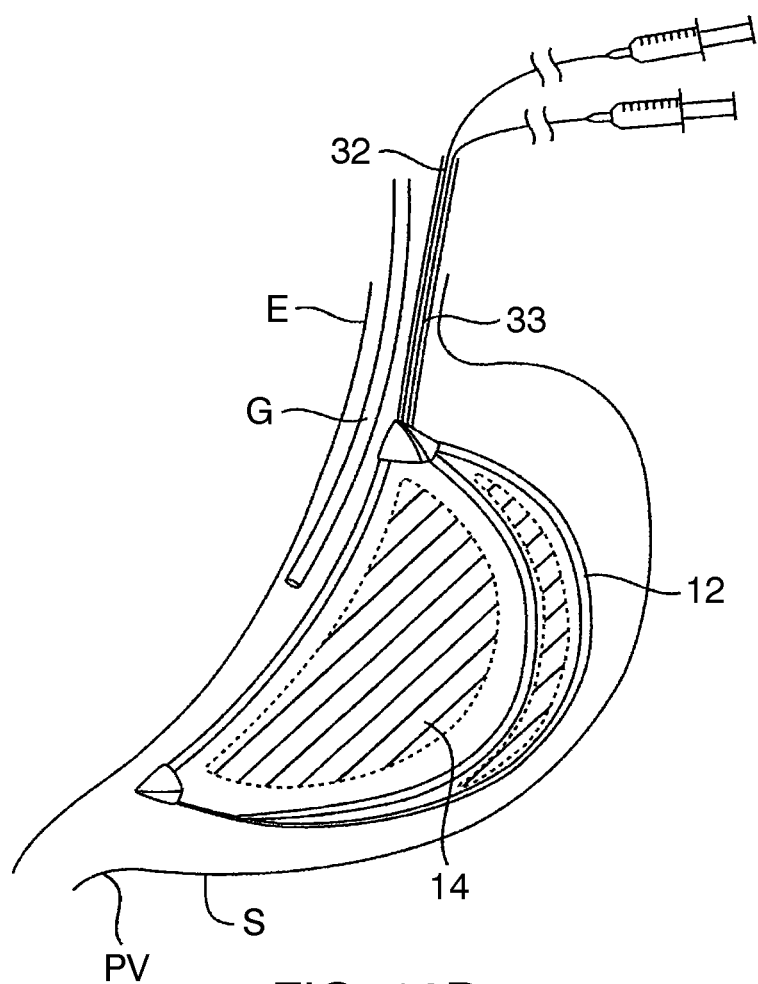

After introducing the gastroscope G, the size of the gastric cavity within stomach S can be estimated and a balloon of an appropriate size selected. The balloon 10 is then also introduced through the esophagus E (orogastrically or nasogastrically) using an appropriate catheter or optionally using the inflation tube(s) which will be used to inflate the balloon. After the entire balloon is confirmed to be in the stomach at a proper orientation, typically using the gastroscope G, the various components of the balloon 10 may be inflated as shown in FIGS. 12C and 12D. First, the inflation tube 32 attached to the port which is coupled to the scaffold 12 is inflated, typically using saline or other incompressible liquid until the scaffold structure becomes relatively rigid, as shown in FIG. 12C. During this inflation, the balloon 10 is held by at least an inflation tube 32 and may optionally be held by additional inflation tube(s) and/or a grasper 32.

After the scaffold 12 has been inflated, an additional syringe is used to inflate the space-filling compartments through a second inflation tube 33, as shown in FIG. 12D. The space-filling compartments, again, will typically be inflated with a combination of saline or other liquid and air or other gas in order to achieve the desired density of the inflation medium therein. The external bladders 16 will be inflated in a similar manner, typically using air or other gas inflation medium only.

Figure 12E:
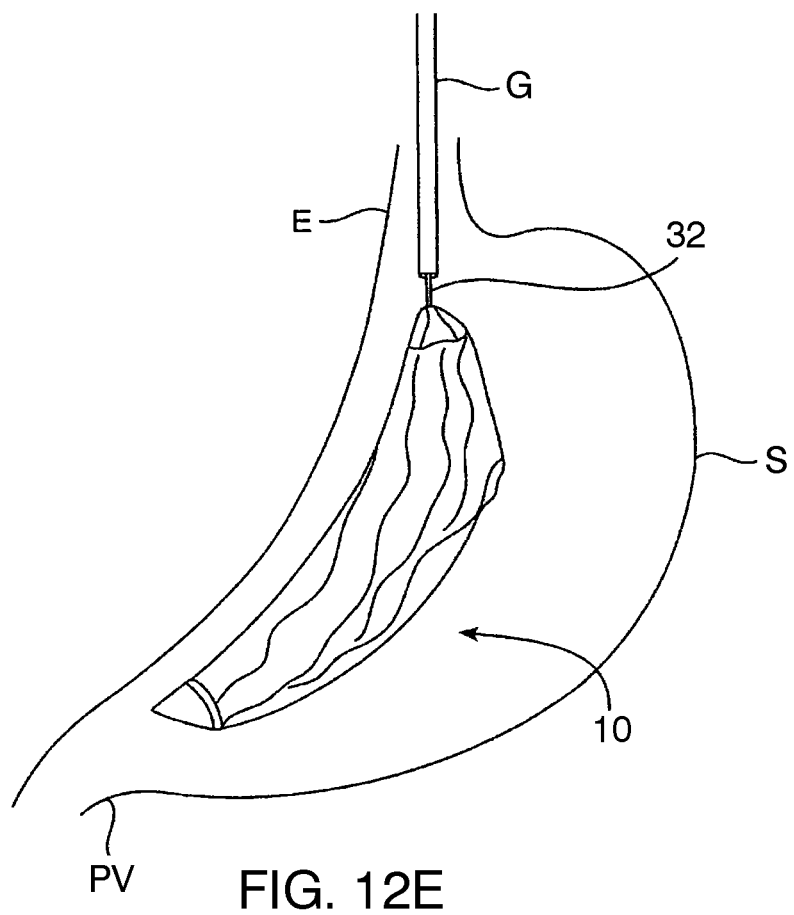

When it is desired to remove the gastric balloon 10, the balloon may be deflated as previously discussed and removed through the esophagus using a grasper 32 passing through the gastroscope G, as shown in FIG. 12E. Typically, the balloon will be pulled out using both the gastroscope and the grasper 32.

Figure 13A:
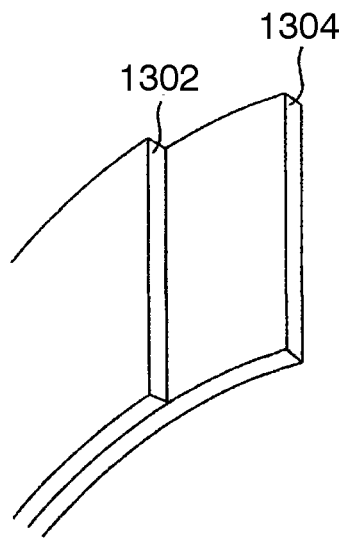
FIGS. 13A through 13C are enlarged, peeled-back, cross-sectional views of a portion of the multi-layered wall of an example gastric balloon constructed in different configurations.

As illustrated in FIG. 13A, the wall of a gastric balloon as described herein includes at the minimum an outermost layer 1302 and innermost layer 1304. The layers may be manufactured by either dipping a mold successively into solutions of different materials that dry and cure or by successive precision injections of materials into a mold. Typically, the outermost layer 1302 is made of one or more materials, such as silicone rubber, selected primarily for their non-abrasiveness, biocompatibility in the stomach, and resistance to an acidic environment. Typically, the innermost layer 1304 is made of materials selected primarily for their resistance to structural fatigue and impermeability to the filling fluid. The inner layer 1304 could have biocompatibility of a shorter duration than the outermost layer. The two layers are either bonded together to function as a single wall or left unbonded such that the layers could slide by each other except at certain attachment points.

Figure 13B:
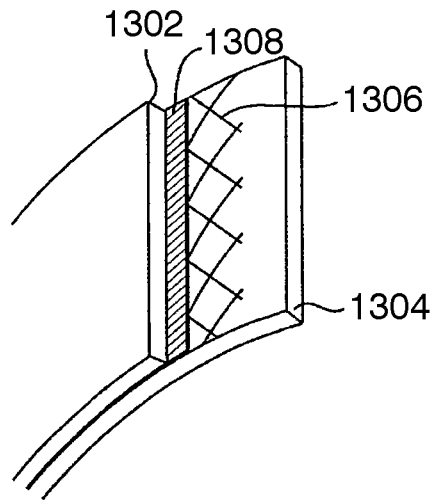

Referring now to FIG. 13B, it may be desirable to enhance the durability further by incorporating other structural elements in the layers, such as a mesh 1306 made of metal, polymer, or high strength fibers, such as Kevlar, or the scaffold (not shown). The mesh could constitute a separate layer as illustrated in FIG. 13B or instead, could be embedded in one of the layers of material, as shown embedded in layer 1304 in FIG. 13C. A mesh 1306 could inhibit the propagation of a tear in the layers. Many of these materials are radio-opaque which enables imaging clearly the entire shape of the device using plain diagnostic X-ray radiography.

Figure 13C:
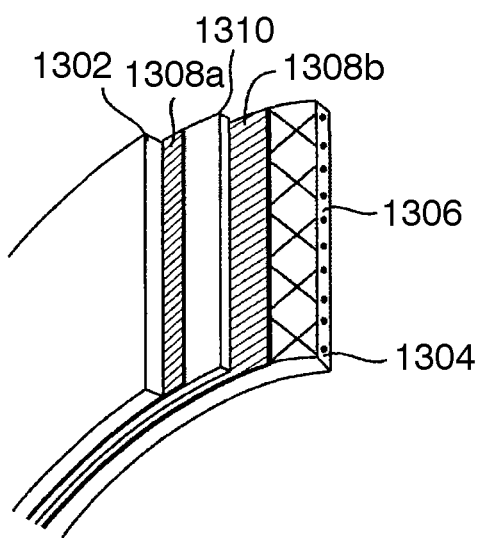

As illustrated in FIGS. 13B and 13C, in addition to layers of 1302 and 1306, one or more layers, 1308 and 1310, of materials selected for the optimal balance of biocompatibility, impermeability, rigidity, shear resistance among other criteria could be added to enhance the structural performance characteristics of the device further.

Figure 14:
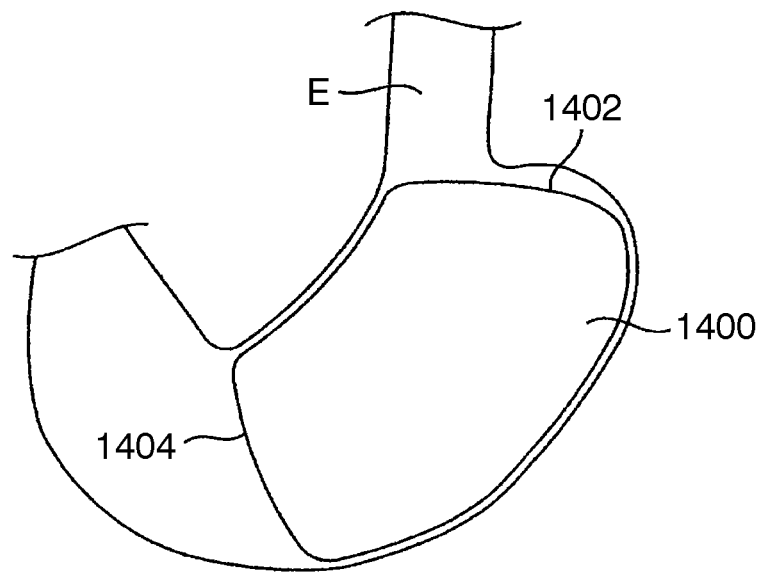
FIG. 14 illustrates another example gastric balloon geometry.

FIG. 14 illustrates an alternative crescent-shaped balloon geometry suitable for use in the gastric balloons of the present invention. Gastric balloon 1400 has a generally flat or truncated upper surface 1402 which is positioned adjacent to the esophagus E. A lower end 1404 is also generally flat or truncated. These flat ends 1402 and 1404 are distinguishable from the more tapered ends of the prior gastric balloon embodiments. Although illustrated schematically as a single unit or structure, it will be appreciated that the balloon 1400 will usually comprise multiple independently inflatable space-filling compartments and optionally further comprise external inflatable bladders. The geometry shown in FIG. 14 is intended to illustrate the peripheral shape of the device including all components.

Figure 15A:
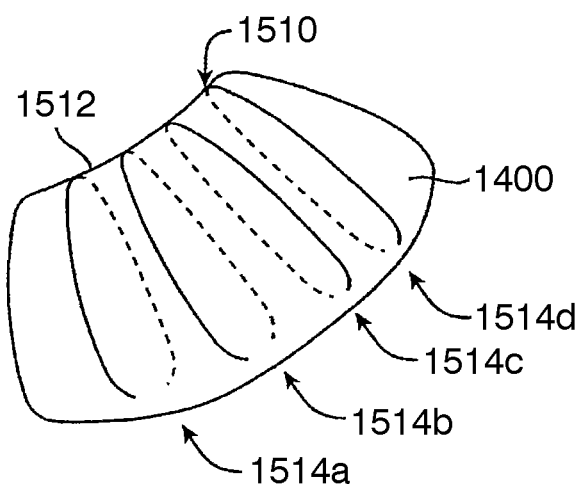
FIG. 15A illustrates a first embodiment of a self-expanding scaffold for the balloon geometry of FIG. 14.
Figure 15B:
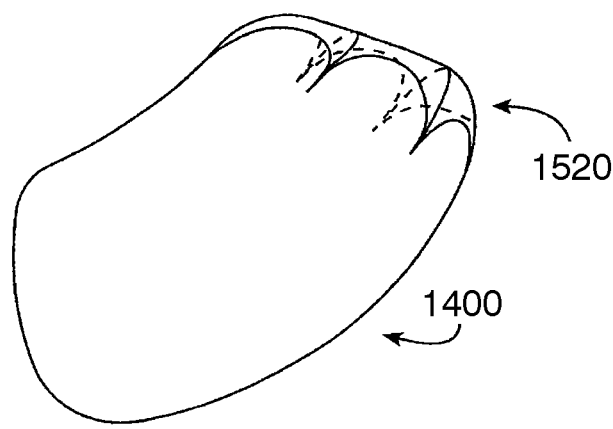
FIG. 15B illustrates a second embodiment of a self-expanding scaffold geometry for a balloon having the geometry of FIG. 14.

Referring now to FIGS. 15A-F, gastric balloon structures having the geometry of balloon 1400 in FIG. 14 may be deployed using a number of different expandable scaffolds. For example, as shown in FIG. 15A, the balloon structure 1400 may include an external "exo-skeleton" 1510 comprising a spine 1512 and a plurality of ribs 1514 extending laterally from the spine. The spine 1512 and ribs 1514 may be made from elastic components, such as nickel titanium alloys or other super elastic materials, permitting them to be folded and compressed to a small width for introduction. The scaffold will then be deployed by releasing the scaffold from constraint after it has been positioned within the stomach.

The balloon 1400 may also be mated with an end cap 1520. The end cap 1520 may include, for example, a plurality of interlaced panels which can be folded down to a low profile configuration for delivery. The panels may be composed of elastic polymers, shape memory metals, shape memory polymers, or the like. The use of end caps 1520 is particularly useful when the balloon will itself comprise a single compartment. The end cap will prevent accidental passage of the balloon through the pylorus even upon rapid deflation of the balloon.

Figure 15C:
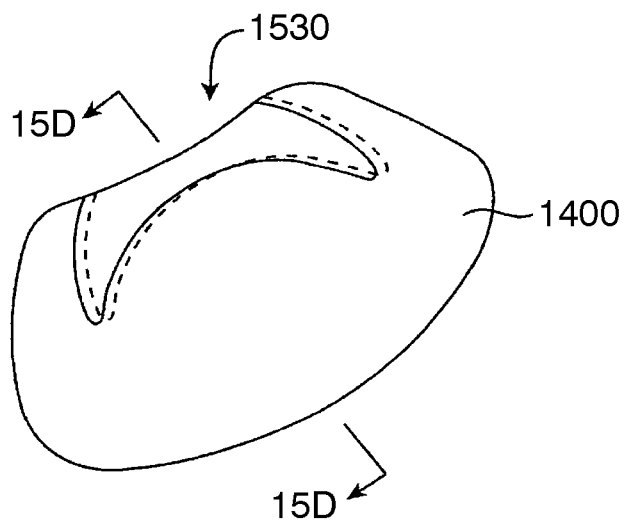
FIG. 15C illustrates an example inflatable scaffold suitable for use with a balloon having the geometry of FIG. 14.

The balloon 1400 may also be mated to an inflatable scaffold 1530, which may be conveniently formed into the shape of a saddle, as shown in FIGS. 15C and 15D. The balloon 1400 may comprise one, two, or more separate inflatable compartments. Each of these compartments, as well as the inflatable scaffold 1530, may require separate inflation, preferably using one of the valving mechanisms described below. The inflatable scaffold 1530 could have other configurations as well, such as being in the form of a lattice with a central inflatable spine and multiple arms disposed laterally outwardly about the remainder of the balloon 1400.

Referring now to FIGS. 15E and 15F, the balloon 1400 may comprise first and second internal inflatable compartments 1540 and 1542 having an external sheath or exoskeleton 1544. The sheath 1544 may be, for example, a non-distensible outer tubular structure having the desired crescent geometry, with the inflatable compartments 1540 and 1542 disposed therein. Alternatively, the exoskeleton could comprise a mesh, fabric, or other flexible containment member which holds the separate inflatable compartments 1540 and 1542 in place relative to each other. At least a portion of the exoskeleton 1544 could be made to be non-collapsible in order to prevent accidental passage of the balloon through the pyloric valve in case of unintended deflation of both of the inflatable compartments 1540 and 1542.

The compartments 1540 and 1542 could also be held together by a spine element 1550, as shown in FIG. 15F. The balloons would be attached to the spine, optionally by heat sealing or adhesives, usually one or more fasteners 1552, such as adhesive straps, are provided about the periphery of the inflatable compartments 1540 and 1542 to hold them together after deployment. The spine 1550 can also optionally be used to receive and deploy inflation tubes, as described in more detail below.

Each of the balloons 1400 described above may be provided with a valve mechanism or assembly to permit selective inflation with liquid fluids, gaseous fluids, or a combination thereof. If only a single inflatable compartment is utilized, the valving mechanism could be simply a one-way valve having a connector for releasably connecting to an inflation tube. For example, the inflation tube could be connected to the connector on the valve prior to introduction of the balloon in the patient's stomach. After introduction, the inflation medium could be introduced through the tube, and the tube detached and removed after inflation is complete. Optionally, the inflation tube could be introduced later for reinflation of the balloon if desired.

When two or more inflatable compartments, and optionally external bladders, are provided, the valve assemblies of the present invention may provide for selectively delivering inflation medium to individual inflation ports on each of the inflatable compartments, external bladders, and optionally inflatable scaffolds. Inflation valves may include a one-way valve structure, such as a flap valve or a duckbill valve. The valves associated with each compartment can be arranged to permit manipulation of an associated inflation tube so that the valve is in line with an inflation port on the inflation tube to permit delivery of inflation medium.

Figure 16:
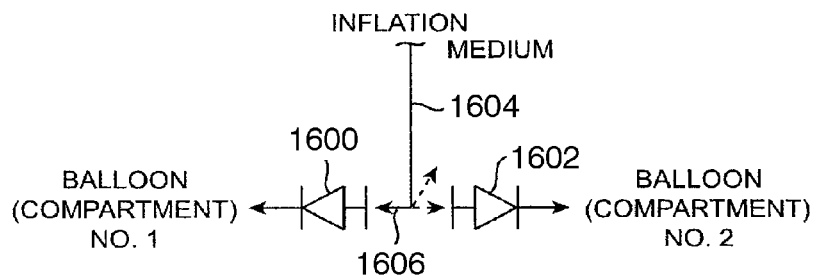
FIGS. 16-18 are flow diagrams illustrating several valving systems suitable for inflating gastric balloons having multiple inflatable compartments and optionally internal bladders.

In FIG. 16, for example, a first one-way valve 1600 can be mounted on a wall of a first balloon compartment and a second one-way valve 1602 can be mounted on the wall of a second balloon compartment. By then arranging the two valves in opposite directions along a common axis, an inflation tube 1604 having a rotatable inflation port 1606 can be disposed between the two valves. Then by turning the inflation tube, the first valve 1600 or the second valve 1602 may be selected to deliver inflation medium through the single inflation tube 1604.

Figures 17, 18:
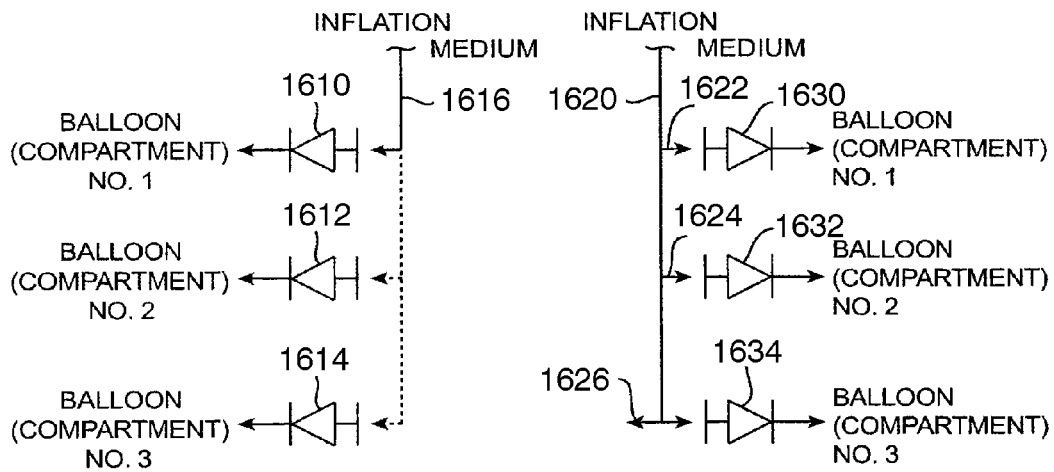

Alternatively, as shown in FIG. 17, a first inflation valve 1610, a second inflation valve 1612, and a third inflation valve 1614, each of which is associated with a respective balloon compartment, may be axially arranged so that a single inflation tube 1616 may be translated to successfully access each of the one-way valves 1610. In this way, each of the associated balloon compartments may be selectively inflated and reinflated by simply axially translating the inflation tube 1616.

As a further alternative, as shown in FIG. 18, a single inflation tube 320 having multiple inflation ports 1622, 1624, and 1626 may be disposed next to a linear array of balloon compartments and one-way inflation valves 1630, 1632, and 1634. In this way, instead of axially translating the inflation tube 1620, the valves can be selected by rotating the tube so that only a single inflation port is aligned with a single one-way valve at one time.

It will be appreciated that the above-described valve mechanisms and assemblies may be constructed in a wide variety of ways using a wide variety of one-way valve structures. For the purposes of the present invention, it is desirable only that the valve structures permit selective introduction of an inflation medium to individual balloon compartments using a single inflation tube. It will also be appreciated that more than one valve may be used in series (not shown) in place of a single valve to reduce further the potential for leakage of the filling media.

Figure 19:
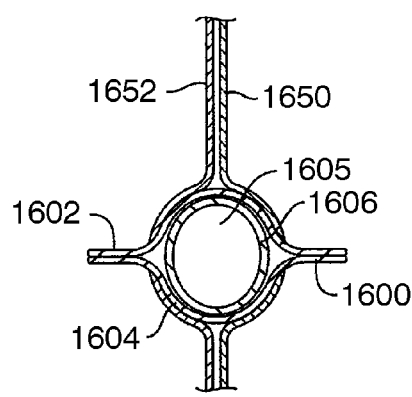
FIG. 19 illustrates an exemplary structure for valving according to FIG. 16.

A first specific structure for implementing the inflation assembly of FIG. 16 is shown in FIG. 19. The inflation tube 1604 having inflation port 1606 is disposed between a wall 1650 of a first balloon and a wall 1652 of a second balloon. The first one-way valve 1600 is positioned through the first wall 1650, and the second one-way valve 1602 is positioned through the second wall 1652. Those valves are shown as duckbill valves. As shown in FIG. 19, the port 1606 is aligned with the first one-way valve 1600 so that introduction of a pressurized inflation medium through lumen 1605 of the inflation tube 1604 will open the duckbill valve and allow inflation medium to enter the first balloon. By then rotating the inflation tube 1650 by 180° so that it is aligned with the second valve 1602, inflation medium can be similarly delivered to the second balloon.

Figure 20A:
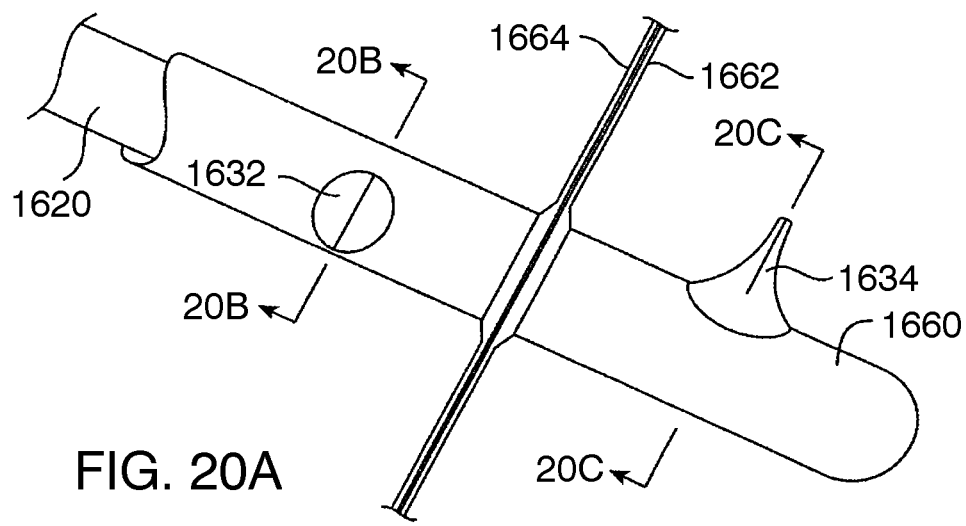
FIGS. 20A-20C illustrate an exemplary structure for valving according to FIG. 18.
Figure 20B:
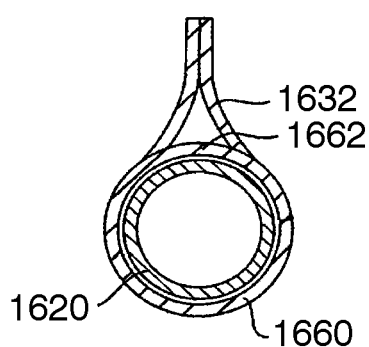
Figure 20C:
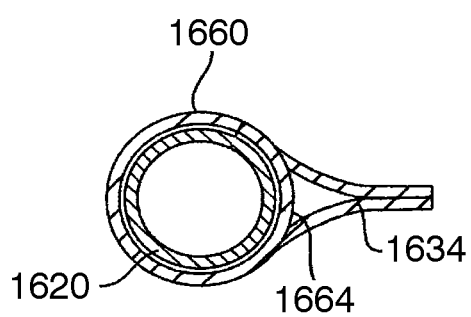

A specific valve system constructed generally as shown in FIG. 18 is shown in FIGS. 20A-20C. The inflation tube 1620 is rotatably disposed within an outer tube 1660 which passes between walls 1662 and 1664 of first and second inflatable compartments, respectively. The distal-most one-way valve 1634 is disposed in a first radial direction on the outer tube 1660, and the next inner one-way valve 1632 is offset by 90°. The ports 1662 and 1664 on the inflation tube 1620 (FIGS. 20B and 20C not illustrated) will be arranged so that in a first rotational position one port 1662 is aligned with one-way valve 1632 and in a second rotational position, a second port 1664 is aligned with one-way valve 1634. At no time, however, is more than one inflation port aligned with more than one one-way valve on the outer tube 1660. Thus, by rotating inflation tube 1620, individual inflatable compartments can be inflated.

While the above is a complete description of the preferred embodiments of the invention, various alternatives, modifications, and equivalents may be used. Therefore, the above description should not be taken as limiting the scope of the invention which is defined by the appended claims.

What is claimed:

1. An obesity treatment device for deploying in a stomach of a patient, comprising:
   a plurality of adjacent, spaced apart inflatable space-filling compartments, wherein each compartment of the plurality of inflatable space-filling compartments has a respective inflated state volume that is maintained during treatment of the patient; and a valve system for introducing a fluid into each compartment of the plurality of inflatable space-filling compartments and for retaining, upon inflation, fluid in the plurality of inflatable space-filling compartments, wherein
the valve system comprises a respective valve structure for introducing fluid into each inflatable space-filling compartment of the plurality of inflatable space-filling compartments, wherein each respective valve structure includes at least a first valve in series with a second valve;
wherein the obesity treatment device is to form, upon at least partially filling the plurality of inflatable space-filling compartments, to a curved shape conforming to a natural three-dimensional kidney shape of the stomach such that an outer surface of the obesity treatment device aligns against greater and lesser curvatures of the stomach.

2. The obesity treatment device of claim 1, wherein the plurality of inflatable space-filling compartments form, when in an inflated state, a cavity therebetween through which food may pass.

3. The obesity treatment device of claim 1, wherein a respective fluid volume for filling each compartment of the plurality of inflatable space-filling compartments leaves in the stomach a residual volume proximal to the obesity treatment device unoccupied by the obesity treatment device during a resting state of the stomach, and wherein said residual volume is 10 ml to 100 ml.

4. The obesity treatment device of claim 1, wherein, upon inflation, the obesity treatment device rests within the stomach without exerting pressure at any point in the stomach sufficient to cause ulceration.

5. The obesity treatment device of claim 1, wherein an outer surface of each of the inflatable space-filling compartments aligns against greater and lesser curvatures of the stomach.

6. The obesity treatment device of claim 5, wherein the obesity treatment device is untethered in the stomach after inflation.

7. The obesity treatment device of claim 1, wherein the first valve structure includes a one-way valve.

8. The obesity treatment device of claim 1, further comprising a flexible central spine structure spanning a gap between and connecting at least a first compartment of the plurality of inflatable space-filling compartments and a second compartment of the plurality of inflatable space-filling compartments, wherein aligning the outer surface of the obesity treatment device against the greater and lesser curvatures of the stomach comprises flexibly conforming the obesity treatment device to the natural three dimensional kidney shape of the stomach through flexing the flexible central spine structure.

9. The obesity treatment device of claim 8, wherein the flexible central spine structure is in fluid communication with the valve system.

10. The obesity treatment device of claim 9, wherein the flexible central spine structure encloses an inflation lumen for introducing the fluid into the plurality of inflatable space-filling compartments.

11. The obesity treatment device of claim 1, wherein fluid in each of the plurality of inflatable space-filling compartments is a same type of fluid.

12. A method for deploying a gastric balloon structure in a gastric cavity of a patient, comprising:
determining one or more dimensions of the gastric cavity in a feeding state;
selecting a respective fill volume for each chamber of a plurality of isolated chambers of the gastric balloon structure;
introducing the gastric balloon structure to the gastric cavity; and
after said introducing, at least partially filling each chamber of the plurality of isolated chambers of the gastric balloon structure with the respective volume of fluid via a valve system of the gastric balloon structure, wherein
the plurality of isolated chambers are non-concentric and adjacent,
at least partially filling each chamber of the plurality of isolated chambers comprises introducing fluid into the respective chamber via a respective valve structure of the valve system, and
a collective volume of the plurality of isolated chambers remaining inflated after deflation of any single chamber of the plurality of isolated chambers prevents the gastric balloon structure from passing through the pyloric valve of the gastric cavity;
wherein the gastric balloon structure, in its inflated state, is to form to a curved shape conforming to a natural three-dimensional kidney shape of the gastric cavity such that an outer surface of the gastric balloon structure aligns against greater and lesser curvatures of the gastric cavity.

13. The method of claim 12, wherein the gastric balloon structure, upon inflation, rests within the gastric cavity without exerting pressure at any point in the gastric cavity sufficient to cause ulceration.

14. The method of claim 12, wherein an outer surface of each of the space-filling compartments aligns against greater and lesser curvatures of the stomach.

15. The method of claim 12, wherein at least partly filling the plurality of isolated chambers comprises:
releasably attaching an inflation tube to the valve system; and
introducing the fluid into a first isolated chamber of the plurality of isolated chambers through the inflation tube.

16. The method of claim 12, wherein introducing the gastric balloon structure to the gastric cavity comprises introducing the gastric balloon structure through an esophagus of the patient.

17. The method of claim 12, wherein a diameter of the gastric balloon structure is no larger than 2 centimeters prior to inflation.

18. The method of claim 12, wherein fluid in each of the plurality of isolated chambers is a same type of fluid.

19. A system for treating obesity, comprising:
a means for conforming a flexible, space-filling structure to a natural kidney shape of a gastric cavity of a patient;
a means for maintaining at least two isolated inflatable regions of the flexible, space-filling structure such that a collective volume of the at least two isolated inflatable regions remaining inflated after deflation of any single isolated inflatable region of the at least two isolated inflatable regions prevents the flexible, space-filling structure from passing through the pylorus of the patient;
a means for introducing a fluid into each of the at least two isolated inflatable regions after positioning the flexible, space-filling structure within the gastric cavity, wherein the means for introducing is configured to be separated from said means for conforming after introducing the fluid; and a means for receiving the fluid into each region of the at least two isolated inflatable regions and for retaining the fluid in each region, wherein the fluid is received from the means for introducing the fluid.

20. The system of claim 19, wherein the means for conforming is configured to leave in the gastric cavity a residual volume proximal to the means for conforming and unoccupied by the means for conforming during a resting state of the gastric cavity, and wherein said residual volume is 10 ml to 100 ml.

21. The system of claim 19, wherein the means for conforming provides for modulated passage of food through the gastric cavity.

22. The system of claim 19, wherein the means for conforming is configured such that, upon inflation, the flexible space-filling structure rests within the gastric cavity without exerting pressure at any point in the gastric cavity sufficient to cause ulceration.

23. The system of claim 22, wherein undue pressure against the gastric cavity is avoided in part through at least one of i) a fill weight of collective volumes of the at least two isolated inflatable regions, ii) a distribution of the overall space-filling structure, and iii) a buoyancy of the fluid.

24. The system of claim 19, wherein the means for receiving the fluid comprises a respective valve structure of each region of the at least two isolated inflatable regions, the respective valve structure comprising at least a first valve and a second valve.

25. The system of claim 19, further comprising a means for flexibly connecting at least a first region of the at least two isolated inflatable regions and a second region of the at least two isolated inflatable regions by spanning a gap between the first region and the second region, thereby forming a cavity between the first region and the second region through which food may pass.

26. The system of claim 25, wherein the means for flexibly connecting at least the first isolated inflatable region and the second isolated inflatable region is in fluid communication with the means for receiving the fluid.

27. The system of claim 25, wherein the means for flexibly connecting comprises a flexible central spine.

28. The system of claim 19, wherein, each of the at least two isolated inflatable regions comprises a respective inner layer and a respective outer layer.

29. The system of claim 28, wherein, for each of the at least two isolated inflatable regions, the respective inner layer is attached to the respective outer layer.

30. The system of claim 19, wherein fluid in each of the at least two isolated inflatable regions is a same type of fluid.

* * * * *